(12) United States Patent
Rubin et al.

(10) Patent No.: US 8,065,508 B2
(45) Date of Patent: Nov. 22, 2011

(54) ACTIVATING APPLICATIONS BASED ON ACCELEROMETER DATA

(75) Inventors: Andrew E. Rubin, Los Altos Hills, CA (US); David P. Conway, Los Altos, CA (US)

(73) Assignee: Google Inc., Mountain View, CA (US)

( * ) Notice: Subject to any disclaimer, the term of this patent is extended or adjusted under 35 U.S.C. 154(b) by 490 days.

(21) Appl. No.: 12/268,279

(22) Filed: Nov. 10, 2008

(65) Prior Publication Data

US 2009/0132197 A1 May 21, 2009

Related U.S. Application Data

(60) Provisional application No. 60/986,873, filed on Nov. 9, 2007.

(51) Int. Cl.
*G06F 15/177* (2006.01)

(52) U.S. Cl. ............................................. 713/1; 713/100

(58) Field of Classification Search ........................ None
See application file for complete search history.

(56) References Cited

U.S. PATENT DOCUMENTS

| | | | |
|---|---|---|---|
| 2005/0046580 A1* | 3/2005 | Miranda-Knapp et al. | ............ 340/686.1 |
| 2006/0253210 A1 | 11/2006 | Rosenberg | |
| 2007/0036348 A1 | 2/2007 | Orr | |
| 2007/0091292 A1* | 4/2007 | Cho et al. | ............ 355/75 |
| 2007/0107068 A1 | 5/2007 | Kelley et al. | |
| 2007/0254271 A1 | 11/2007 | Burlik et al. | |
| 2009/0247144 A1 | 10/2009 | Jin et al. | |
| 2010/0128007 A1 | 5/2010 | Cole | |

FOREIGN PATENT DOCUMENTS

| | | |
|---|---|---|
| KR | 10-2006-0114511 | 11/2006 |
| KR | 10-2007-0056673 | 1/2007 |
| KR | 10-2007-0035555 | 7/2007 |

OTHER PUBLICATIONS

International Preliminary Report on Patentability for Application No. PCT/US2008/083031, dated May 20, 2010, 6 pages.
International Search Report & Written Opinion for Application No. PCT/US2008/083031, dated May 29, 2010, 11 pages.

* cited by examiner

*Primary Examiner* — Dennis M Butler
(74) *Attorney, Agent, or Firm* — Fish & Richardson P.C.

(57) ABSTRACT

In some implementations, a computer-implemented method includes storing a plurality of acceleration profiles in a mobile device; receiving accelerometer data from an accelerometer in the mobile device; correlating the accelerometer data with one accelerometer profile in the plurality of accelerometer profiles; and activating a user application of the mobile device that is associated with the correlated accelerometer profile. Each acceleration profile can correspond to a sequence of acceleration forces a mobile device would be subjected to when carried with a user during an activity that corresponds to the correlated acceleration profile.

26 Claims, 17 Drawing Sheets

| Activity Nicknames *302* | Applications *304* | Time Filter *322* | Location Filter *340* | Acceleration Profiles *306* |
|---|---|---|---|---|
| Driving in a vehicle *306* |   *312* *314* | | | Profile 140 / Profile 150 |
| Riding on a train *316* |   *318* *328* | AM *324* | | Profile 130 |
| Riding on a train *326* |  *330* | PM *332* | | Profile 130 |
| Walking *334* |  *312* | | | Profile 120 |
| Walking, followed by device being set down *344* |  *320* | | | Profile 120 → Profile 180 |
| Jogging *336* |  *328* | | Home *342* | Profile 110 |

ACTIVATING APPLICATIONS BASED ON ACCELEROMETER DATA

CROSS-REFERENCE TO RELATED APPLICATIONS

This application claims priority under 35 USC §119(e) to U.S. Provisional Patent Application Ser. No. 60/986,873, filed on Nov. 9, 2007, the entire contents of which are hereby incorporated by reference.

TECHNICAL FIELD

This document generally describes systems and techniques for automatically activating applications in a mobile device, and in particular, automatically activating applications based on acceleration data that can be captured by an accelerometer in the mobile device.

BACKGROUND

Many people carry with them various kinds of mobile computing devices (e.g., smartphones, personal digital assistants (PDAs), cell phones, media players, etc.), and they may use their mobile computing devices throughout the day to receive or process information or media content or to communicate with others. For example, a smartphone user may employ the smartphone to play music during a morning jog, provide news during a commute, or manage email, text and voice communications at an office. A PDA user may employ the PDA to display calendar information during a walk from a parking garage to an office, or to provide map information during regular field calls.

SUMMARY

This document describes systems and techniques for automatically activating applications on a mobile device based on a comparison of current real-time acceleration data measured by the mobile device and acceleration profiles that are stored in the mobile device. Each stored acceleration profile can be associated with an activity that the user may engage in while using the corresponding mobile device application. For example, as described by way of background above, a jogger may use a media player application provided by his or her smartphone to listen to music while jogging. The smartphone can detect when the jogger starts jogging, for example, based on detecting the real-time acceleration data that matches an acceleration profile stored on the mobile device that is associated with jogging and with the media player application.

The details of one or more implementations are set forth in the accompanying drawings and the description below. Other features, objects, and advantages will be apparent from the description and drawings, and from the claims.

DESCRIPTION OF DRAWINGS

FIGS. 1A-1H illustrate example acceleration profiles that correspond to various activities that a mobile device user may engage in.

Like reference symbols in the various drawings indicate like elements.

DETAILED DESCRIPTION

Figure 1A:
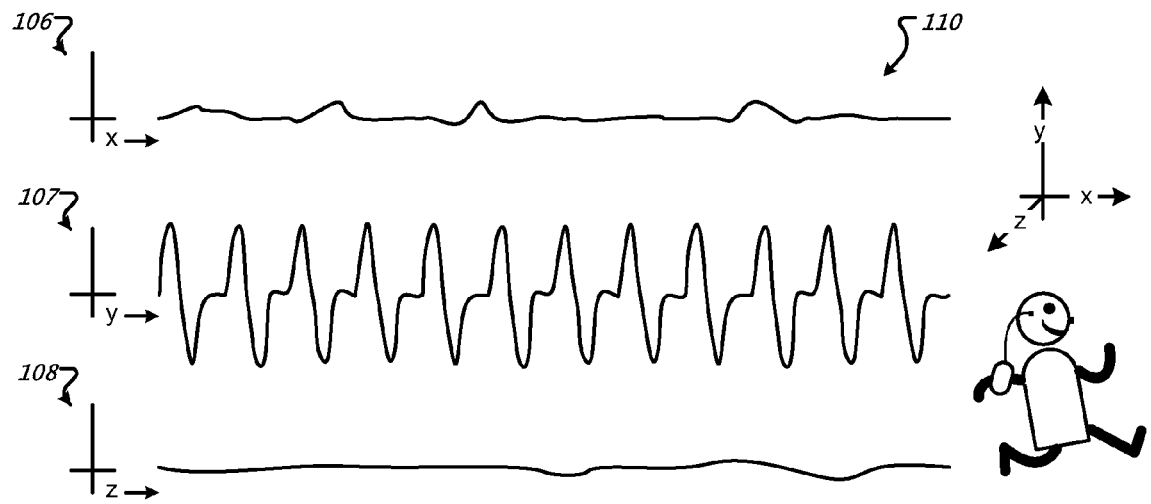

This document describes systems and techniques for automatically activating applications on a mobile device based on a comparison of current real-time acceleration data measured by the mobile device and acceleration profiles that are stored in the mobile device. Each stored acceleration profile can be associated with an activity that the user may engage in while using the corresponding mobile device application. For example, a jogger may use a media player application provided by his or her smartphone to listen to music while jogging. The smartphone can detect when the jogger starts jogging, for example, based on detecting the real-time acceleration data that matches an acceleration profile stored on the mobile device that is associated with jogging and with the media player application.

The mobile device can store a number of different acceleration profiles, each of which may correspond to a different activity and may be associated with a corresponding application that the mobile device user may run while engaging in that activity. In particular, one acceleration profile may store data indicative of a jogging motion, and that profile may be associated with a music application.

In some implementations, stored acceleration profiles are provided with the mobile device (e.g., preloaded when the mobile device is delivered to its initial end-user). In particular, for example, acceleration profiles that may be generic to many different users or mobile devices, such that a mobile device will readily determine when real-time acceleration data captured by the mobile device matches one of the stored acceleration profiles, may be preloaded in a mobile device, or otherwise accessible to the device. Such profiles may be advantageously employed to detect, for example, common motions or activities whose acceleration data may not exhibit much user-to-user or device-to-device variation (e.g., highway travel, as described below with reference to FIG. 1E; elevator travel, as described below with reference to FIG. 1F; etc.).

Some generic acceleration profiles may be generated by analyzing various types of devices (e.g., including the mobile device in which the generic profiles are preloaded, or various other devices other the mobile device where the profiles may be averaged to account for differences between the various devices). In some implementations, generic acceleration profiles can be stored in the mobile device after the device is delivered to the initial end-use. In particular, for example, acceleration profiles can be downloaded to the mobile device or otherwise transferred to the mobile device (e.g., by a cable from another device, by a removable storage device, etc.).

In some implementations, various available acceleration profiles may be scanned for a possible match to acceleration data captured by a mobile device. For example, as a mobile device captures acceleration data, the acceleration data may be compared (e.g., in real time, or substantially real time) to network-accessible profiles. Libraries or databases of such profiles may be publicly available, or certain profiles may be available in a semi-private or private manner (e.g., from an access-controlled service). Network-accessible profiles (or profiles that are accessible in some other manner, such as profiles on a removable storage device) may be scanned and compared to the real-time acceleration data from the device in a particular order—such as an order based on profile information associated with the mobile device, or an order based on other devices or users associated with the mobile device (e.g., via buddy lists or other social or functional connections) from which the real-time acceleration data was obtained.

In some implementations, acceleration profiles can be recorded by and stored in the mobile device (e.g., such that the recorded acceleration profiles are customized to a particular mobile device or a particular user of that mobile device).

In operation, the mobile device can capture real-time acceleration data (e.g., with an accelerometer) and compare the real-time acceleration data with acceleration profiles stored in the mobile device. If the mobile device determines that real-time acceleration data corresponds to (e.g., matches, based on a comparison algorithm and a measure of similarity determined by the comparison algorithm that falls within a threshold measure of similarity (e.g., a statistical measure of similarity of at least 80%, 90%, or 95%; a greater similarity by at least 10%, 15%, etc., between the real-time data an acceleration profile determined to be matching that between the real-time data and any other acceleration profile; etc.)) an acceleration profile (e.g., an acceleration profile for jogging), the mobile device can automatically activate an application associated with the matching acceleration profile (e.g., a media player application). The process of receiving real-time acceleration data and comparing it to previously stored acceleration profiles is described in greater detail below with reference to FIG. 2A.

The association between an acceleration profile and an application can be configurable by the user, such that the user can determine certain applications that are to be activated when certain activities are detected. Associating applications to acceleration profiles is described in greater detail below with reference to FIGS. 3A and 3B.

Real-time acceleration data and stored acceleration profiles can include data received from an accelerometer. Different kinds of accelerometers can provide different kinds of data, but in general, some accelerometers measure force in one or more directions, and in particular, many accelerometers measure force in three directions—namely, along an x-axis, a y-axis and a z-axis. From force data, acceleration, velocity and position data may be determined. For example, with a three-axis accelerometer, position of the accelerometer can be determined based on which axis measures gravitation force. In some implementations, acceleration data can be provided by a three-axis linear accelerometer (e.g., a MEMS-based accelerometer (microelectromechanical systems) that can output force data in three different axes at a rate of 100-400 Hz). Other devices can also provide acceleration data.

In some implementations, an acceleration profile stores a collection of acceleration data. Acceleration data can include force data corresponding to each of three axes for some period of time. For simplicity, force and acceleration may be used interchangeably herein, but the reader will appreciate that accelerometers generally measure force, and that from the force data and the mass of accelerometer components, acceleration values can be determined. Various examples of acceleration data for different activities are described with reference to FIGS. 1A-1H.

For purposes of example, raw data in three different axes (e.g., an x-axis 106, a y-axis 107, and a z-axis 108) is graphically depicted in FIGS. 1A-1H. In actual implementations, the raw data can include a time-ordered series of numbers corresponding to force values in each direction (e.g., $\{(F_{1x}, F_{1y}, F_{1z}), (F_{2x}, F_{2y}, F_{2z}), \ldots, (F_{nx}, F_{ny}, F_{nz}), \ldots\}$, where new force values are provided at a regular time interval, such as every 2.5 ms or at some other frequency that facilitates generation of acceleration profiles). In other implementations, two-axis or one-axis accelerometers can provide acceleration data, or a device other than an accelerometer can be employed to provide data indicative of an acceleration or motion profile.

FIG. 1A illustrates acceleration data 110 that may correspond to a mobile device carried by a user who is jogging or running. For the sake of this description, axes can be defined as depicted in FIG. 1A. In particular, an x-axis 106 can correspond to a line that lies on a horizontal plane relative to the jogger and that is in-line with the forward path along which the jogger travels; a y-axis 107 can correspond to a vertical plane of the jogger, and a z-axis 108 can correspond to a horizontal plane of the jogger in a direction that is perpendicular to the x-axis 106. Based on this orientation, data captured along the x-axis can measure the forward acceleration (e.g., the speeding up or slowing down of the jogger); data captured along the y-axis 107 can measure vertical acceleration (e.g., a jogger's bounce); and data captured along the z-axis 108 can measure a side-to-side acceleration (e.g., the jogger's sway).

For a jogger who is jogging at a relatively constant pace and in a relatively straight line, x-axis 106 (e.g., forward) acceleration values may be relatively constant; y-axis 107 (e.g., vertical) acceleration values may indicate a base force associated with gravitation and a periodic acceleration and deceleration from the jogger's vertical bounce; and z-axis 108 (e.g., side-to-side) acceleration values may be relatively constant. The frequency of the y-axis component can correspond to a step rate of the user, and the amplitude of the y-axis component can correspond to a force with which the user steps. Amplitude and frequency may both be higher in the case of a user who is jogging or running rather than walking. For purposes of example and comparison, example acceleration for a user who is walking is shown in FIG. 1B.

Figure 1B:
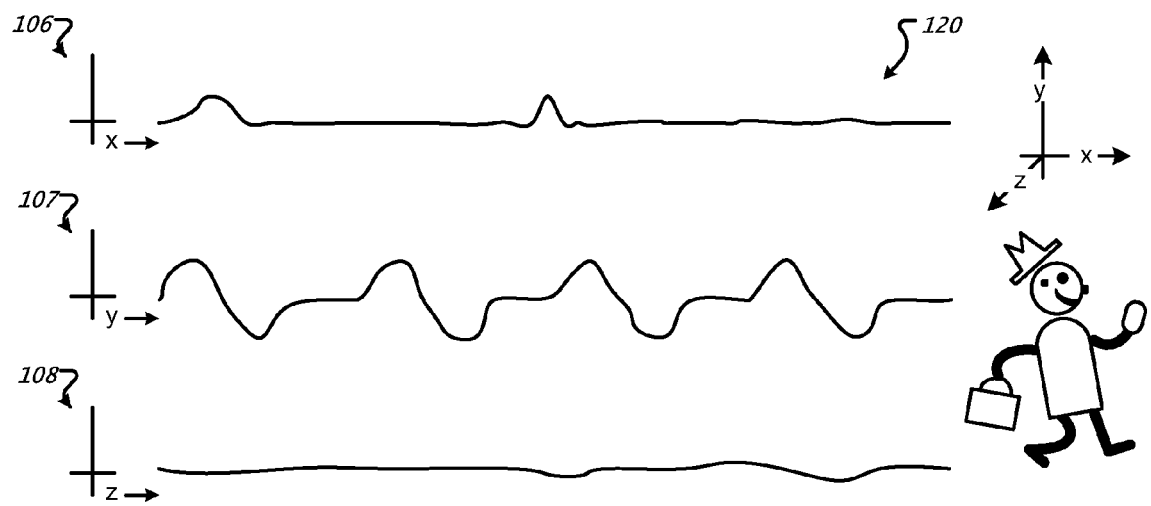

FIG. 1B illustrates example acceleration data 120 that can correspond to a mobile device carried by a user who is walking. Like a jogger who is jogging at a relatively constant pace in a relatively straight line, a walker doing the same may experience little acceleration along the x-axis 106 or the z-axis 108 (e.g., except for occasional increases or decreases in pace, or swerves to one side of the other). Along the y-axis 107, the acceleration 110 shows a periodic acceleration and deceleration corresponding to a small amount of vertical movement associated with the user's stride. The frequency of the periodic acceleration can correspond to the user's step rate. As depicted in FIG. 1B, the amplitude of the y-axis 107 data can be smaller than y-axis data associated with jogging, given that walking steps are usually softer (e.g., have less impact) that jogging or running steps. Various other example acceleration profiles are now described.

Figure 1C:
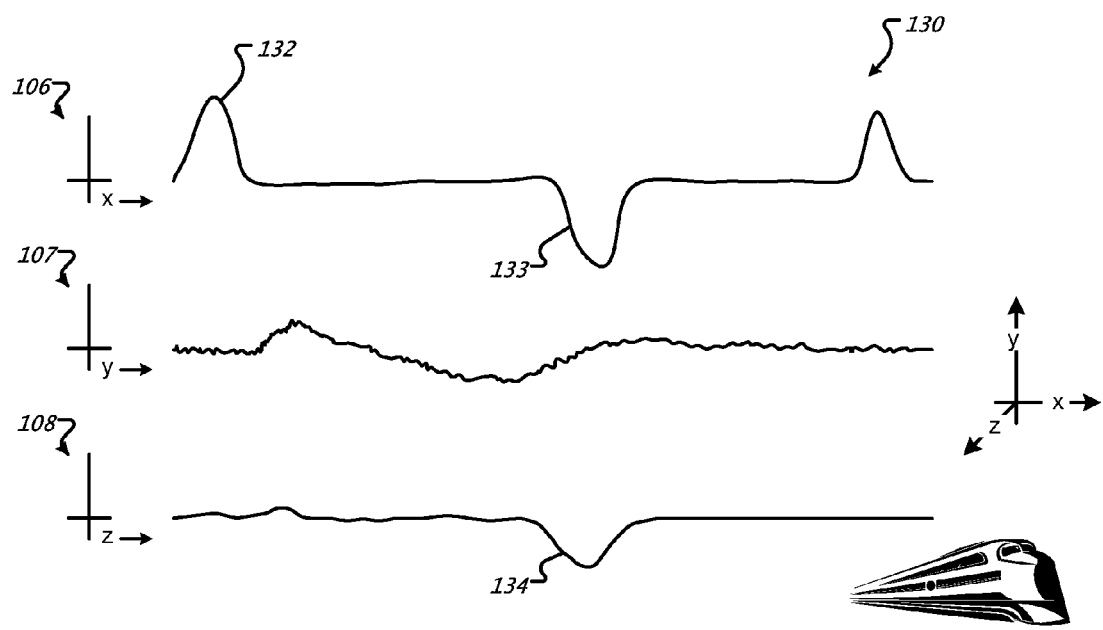

FIG. 1C illustrates example acceleration data 130 that can correspond to a mobile device carried by a user who is riding a train. As depicted in FIG. 1C, a train may subject the mobile device to periodic acceleration 132 and deceleration 133 forces along the x-axis 106 as the train departs from and arrives at stops on its route. Along the y-axis 107, the train may subject the mobile device to acceleration and deceleration as it ascends and descends inclines on its route. In addition, the mobile device may detect higher frequency acceleration along the y-axis 107 as the train travels over regular seams or breaks in the rails on which it rides. The mobile device may also detect acceleration forces 134 along the z-axis 108, for example, as the train traverses relatively sharp curves in the rails.

Figure 1D:
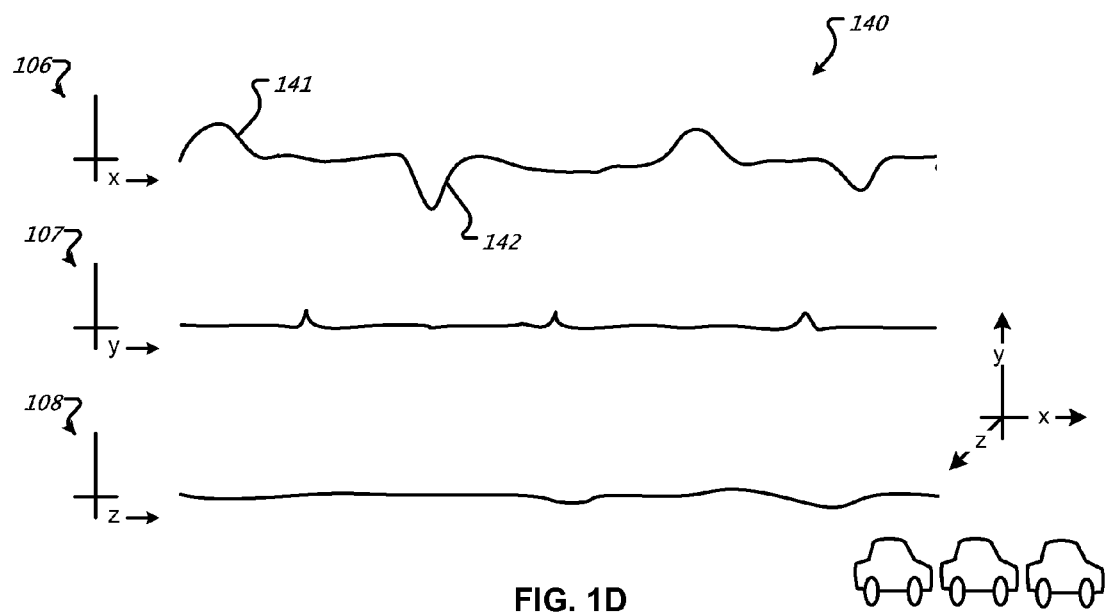

FIG. 1D illustrates example acceleration data 140 that can correspond to a mobile device carried by a user who is in a vehicle in heavy traffic (e.g., stop-and-go traffic). As depicted in FIG. 1D, stop-and-go traffic can cause frequent, possibly gradual, acceleration 141 and deceleration 142 along the x-axis 106 of a vehicle in the traffic (and correspondingly, in a mobile device in the vehicle), which may be associated with the starts and stops (or slow-downs and speed-ups) that an automobile performs in stop-and-go traffic. A small amount of periodic acceleration along the y-axis 107 may be associated with road expansion joints. Acceleration along the z-axis 108 may be negligible, absent any swerves by the vehicle.

Figure 1E:
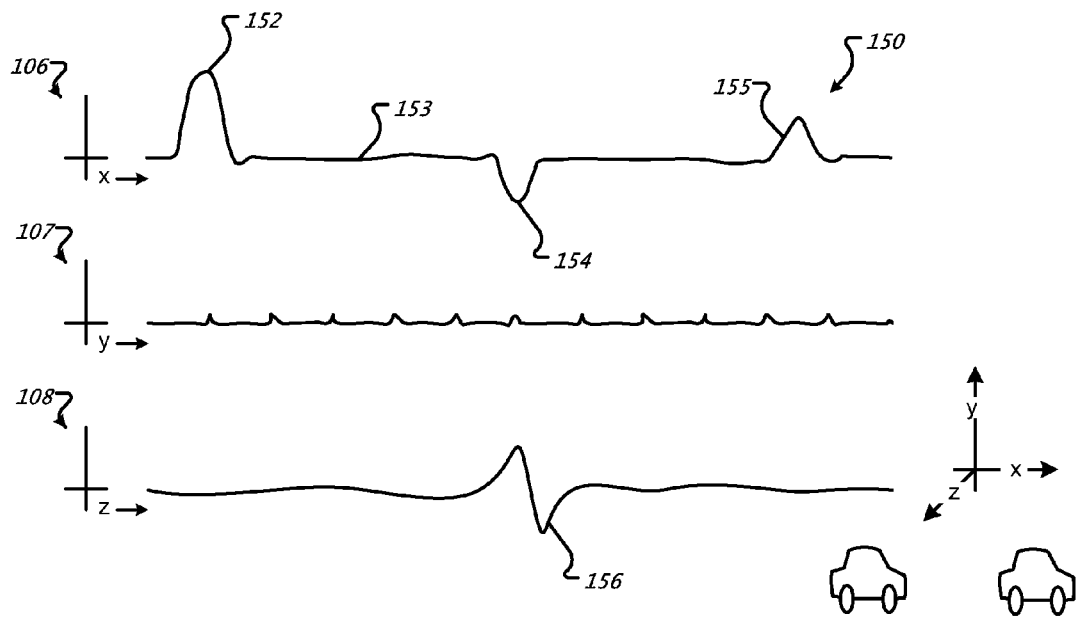

FIG. 1E illustrates example acceleration data 150 that can correspond to a mobile device carried by a user who is in a vehicle in light traffic (e.g., smooth-flowing traffic traveling at highway speeds). In particular, FIG. 1E depicts along the x-axis 106, for example, initial acceleration 152 followed by a steady cruising speed 153 (no acceleration), then a sudden but brief slow-down 154, then a quick acceleration 155. Along the y-axis 107, the acceleration data can include a high-frequency component associated with highway expansion joints. Along the z-axis 108, the acceleration data is shown as relatively constant, except for a swerve 156 corresponding to the brief slowdown.

Figure 1F:
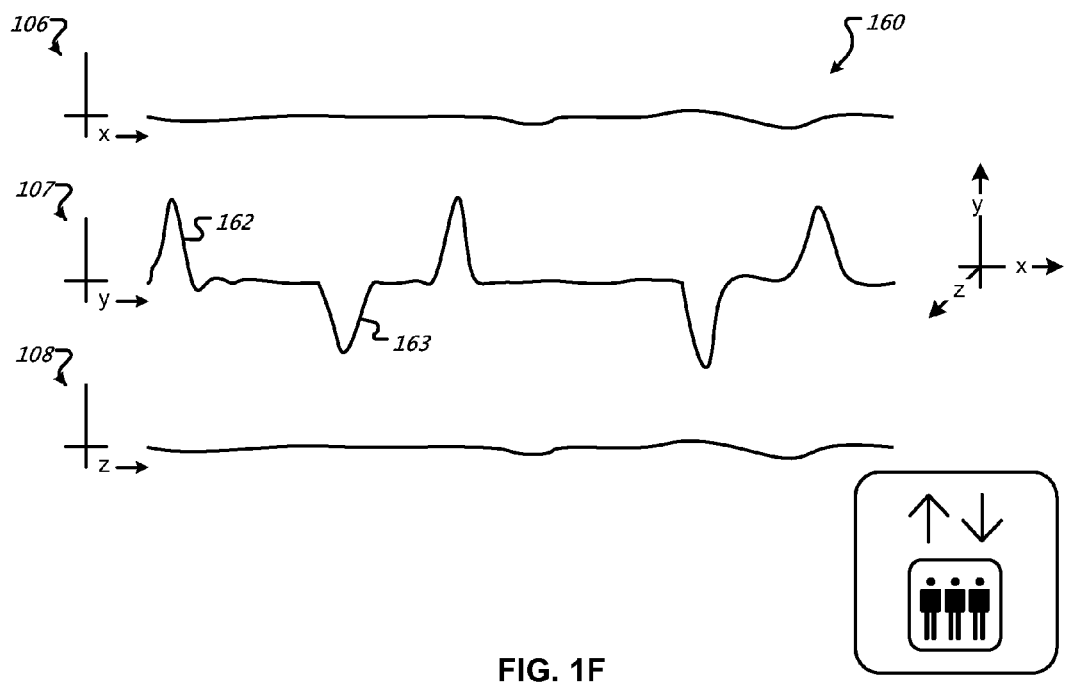

FIG. 1F illustrates example acceleration data 160 that can correspond to a mobile device carried by a user who is riding in an elevator. In particular, FIG. 1F depicts minimal acceleration along the x-axis 106 and z-axis 108 (forward or lateral movement, respectively). The relatively large-amplitude acceleration 162 and deceleration 163 along the y-axis 107 can correspond to starts and stops, respectively, of the elevator on different floors.

Figure 1G:
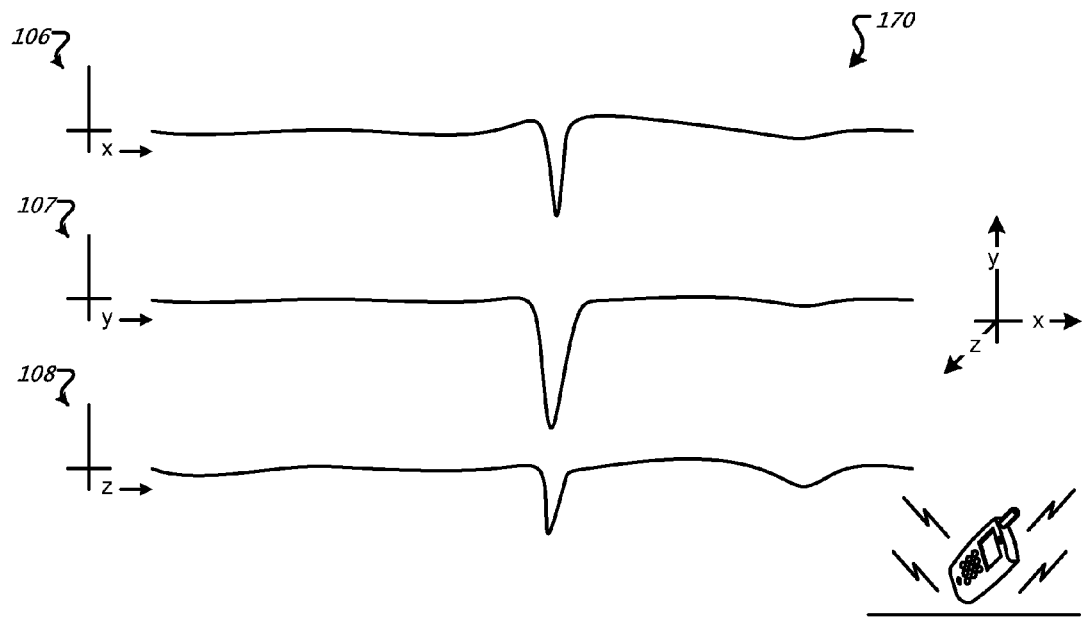

FIG. 1G illustrates example acceleration data 170 that can correspond to a mobile device being dropped. In particular, FIG. 1G depicts the mobile device being dropped at an angle relative the axes, leading to an a sharp deceleration acceleration component that, in this example, is reflected in each axis.

Figure 1H:
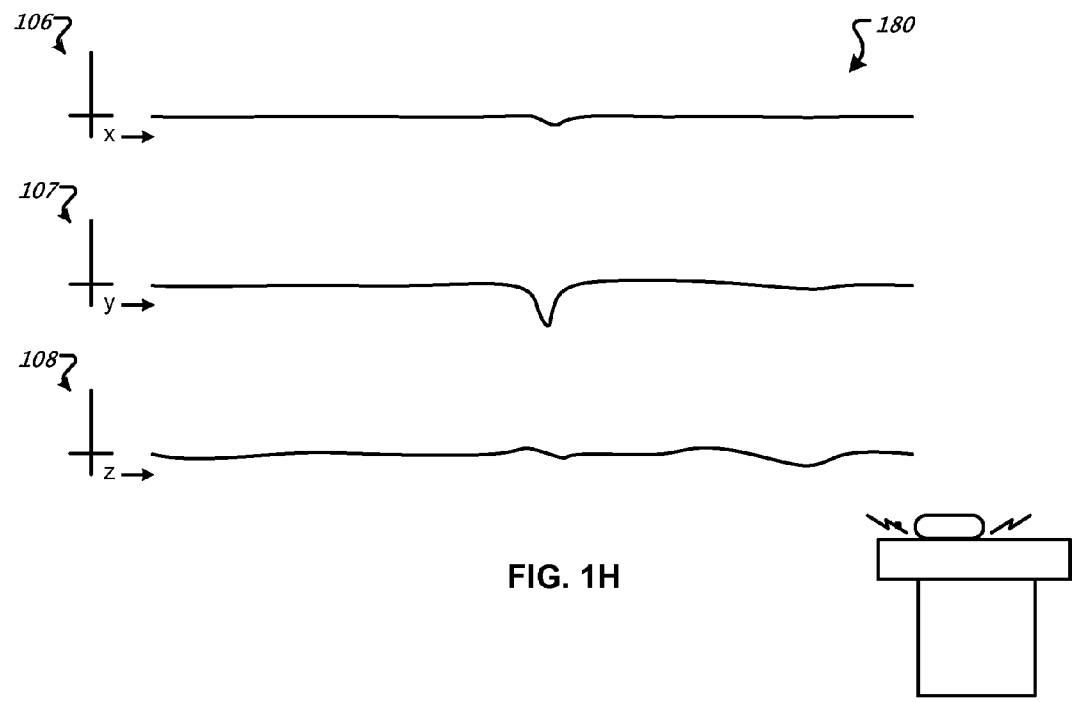

FIG. 1H illustrates example acceleration data 180 that can correspond to a mobile device being set down on a hard surface (e.g., a desk). In particular, a sharp deceleration is depicted along the y-axis 107, with a very small x-axis 106 component. In this example, deceleration forces are depicted as primarily focused along the y-axis 107 (since the mobile device is likely to be set down flat), in contrast to the deceleration forces depicted in FIG. 1G, where the mobile device has been dropped at an angle. Moreover, the deceleration forces depicted in FIG. 1H have a lower magnitude than the deceleration forces depicted in FIG. 1G, since setting the mobile device down on a hard surface will likely subject the mobile device to less force than dropping the mobile device.

For purposes of illustration, FIGS. 1A-H show examples of acceleration data for a mobile computing device that depict the device as oriented such that data along the x-axis 106 corresponds to motion in a generally forward direction, data along the y-axis 107 corresponds to motion in a generally vertical direction, and data along the z-axis 108 corresponds to motion in a generally transverse horizontal direction. The reader will appreciate, however, that a mobile computing device may be positioned in any manner relative to the user or a vehicle in which the user is traveling. Accordingly, acceleration data may be detected along different axes than shown, or along multiple axes in combination. In some implementations, a three-axis accelerometer (or corresponding circuitry) is configured to extract from raw acceleration data acceleration values along three orthogonal axes, regardless of the orientation of the mobile device (e.g., mathematically translate the acceleration data to a different set of axes, as necessary).

Processing acceleration data (e.g., translating the data to a different (e.g., normalized) coordinate system) can have advantages, for example, in cases in which a mobile device is regularly subjected to acceleration forces that correspond to one or more particular profiles, but where the mobile device may have a different orientation each time it is subjected to such forces. In particular, for example, a mobile device that is carried in a purse, handbag, briefcase or laptop bag; or a mobile device resting on the seat or console of an automobile, may be regularly subjected to acceleration forces associated with various activities described below with reference to FIGS. 1A-1H (e.g., walking; travel by automobile, train or elevator; etc.), but the device may be differently positioned each time the corresponding forces are detected. By translating the acceleration data, profiles may be advantageously matched and employed without requiring a user to maintain the mobile device in a particular position or orientation.

Acceleration data can be processed or translated in a number of ways. For example, data from a multi-axis accelerometer can be analyzed to determine deltas between particular points or sequences of points (e.g., to calculate short-term or time-averaged derivatives across various axes). The deltas or derivatives can be analyzed or further processes as described in this document. Raw accelerometer data can be processed in various other ways (e.g., other mathematical functions can be applied: in particular, second derivatives can be calculated and employed; signal processing functions, such as discrete Fourier transforms, can be applied; etc.). In general, the acceleration data may be processed in various ways to remove effects of the same acceleration forces being detected in two axes or all three axes (e.g., because of mobile device orientation).

As shown with reference to FIGS. 1A-H, many activities can have similar acceleration profiles. For example, jogging, as shown in FIG. 1A, and walking, as shown in FIG. 1B, can produce similar acceleration forces along the y-axis 107, and only small (and similar) forces along the x-axis 106 or z-axis 108. In the example data illustrated in FIGS. 1A-B, the distinction between walking and jogging along the y-axis 107 can include an increased frequency of acceleration and deceleration cycles for jogging (e.g., a faster step rate), as well as an increased amplitude (increased force in the vertical direction, or put another way, a harder step).

As another example, acceleration data corresponding to the mobile device being dropped (see FIG. 1G), and acceleration data corresponding to the mobile device being set down on a hard surface (see FIG. 1H) can be similar impulse-like response along one or more axes. However, the acceleration forces associated with a drop may be greater in magnitude and may be seen in more than one axis (e.g., given the likelihood that the device will drop at some angle, such that sharp forces are detected along multiples axes), whereas acceleration forces associated with the mobile device being set down may be smaller in magnitude and may be more likely to be seen primarily along a single axis.

As another example, acceleration forces associated with a train (see FIG. 1C) may be similar to acceleration forces associated with a vehicle. However, greater acceleration forces along the z-axis (e.g., corresponding to transverse motion) may be associated with the train going around corners that are sharper than those a vehicle may navigate.

Figure 2A:
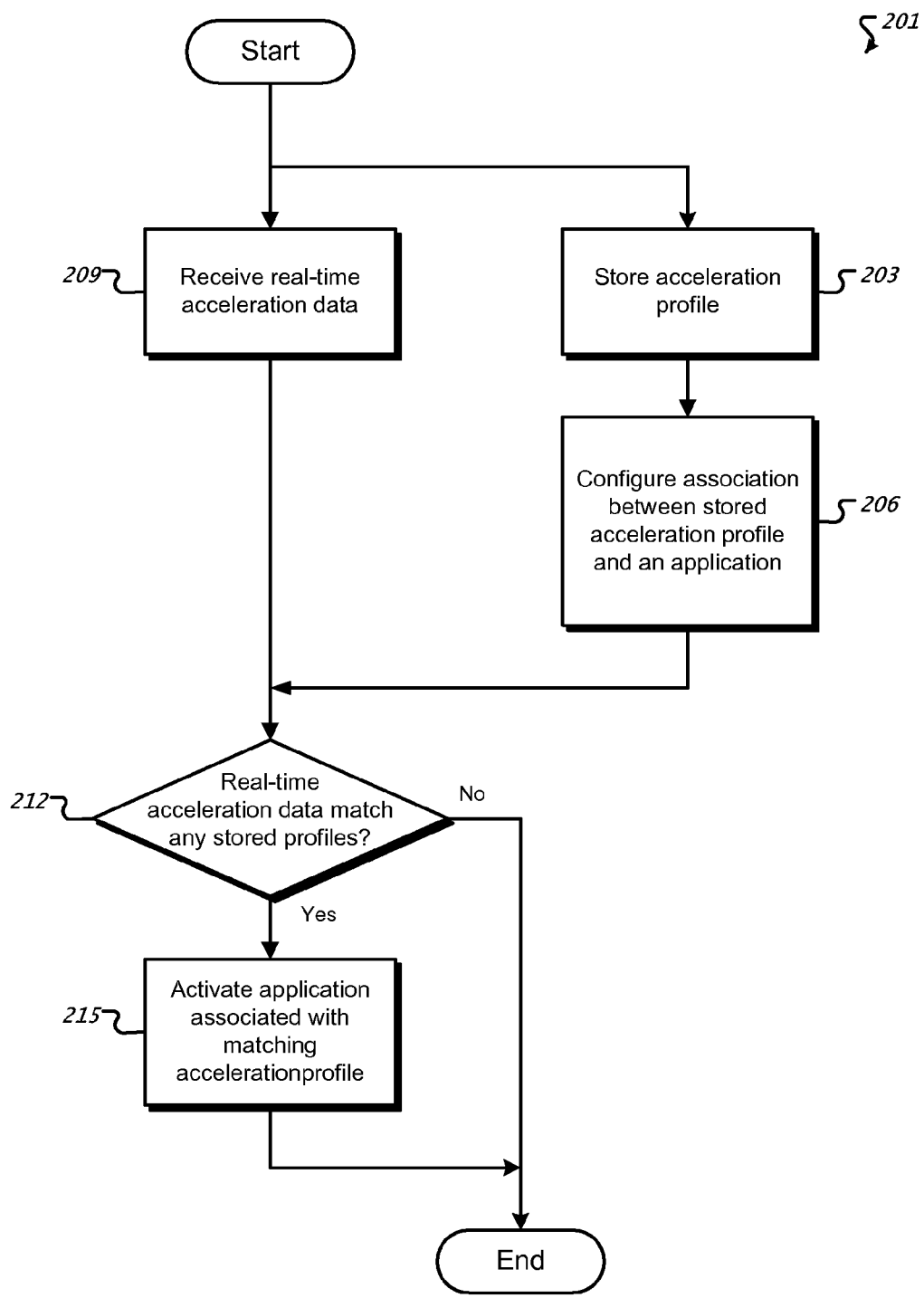
FIG. 2A illustrates an example method of activating applications in response to real-time acceleration data captured by a mobile device.

FIG. 2A illustrates an example method 201 of activating applications in response to acceleration data captured by a mobile device in real-time. In some implementations, an acceleration profile is stored (203) in the mobile device. For example, various acceleration profiles, such as those illustrated in and described with reference to FIGS. 1A-1H can be stored in the mobile device. The acceleration profiles can be pre-stored in the mobile device when it is delivered to the end-user; the acceleration profiles can be downloaded to the mobile device by the end-user; the acceleration profiles can be stored in a network-accessible location or on a removable storage device and accessed in substantially real time (e.g., much like metadata databases associated with media files, which can be employed to provide information (e.g., artist, title, track, copyright information, etc.) about a media file being played or otherwise processed); the acceleration profiles can be captured (e.g., recorded) by the mobile device; etc.

An association can be configured (206) between the acceleration profile and an application that is to be activated when real-time acceleration data is received (209) that is determined to match (212) the stored acceleration profile. In some implementations, the association is made in a configuration mode (e.g., using a configuration interface such as that described below with reference to FIG. 3B or 3C).

Real-time acceleration data can be captured (209) by the mobile device. For example, in some implementations, an accelerometer in the mobile device continuously captures acceleration data (or substantially continuously captures acceleration data at a sampling rate of 25 Hz, 50 Hz, 100 Hz, 400 HZ—to name a few example sampling rates). In some implementations, the captured real-time acceleration data is stored in a circular buffer (or other memory structure) that stores some amount of acceleration data (e.g., 5 seconds of data, 30 seconds of data, 2 minutes of data, 10 minutes of data, 1 hour of data, etc.).

The method 201 can include determining (212) whether the captured real-time acceleration data matches any of the stored (or accessible) acceleration profiles. In particular, for example, a comparison algorithm can be applied between the real-time acceleration data and each of any acceleration profiles that are stored in the mobile device. If no match is found between the real-time acceleration data and any of the acceleration profiles, nor further action may be taken (that is, no applications may be activated; however, the entire method 201 may be periodically repeated with a portion of the real-time acceleration data, as described below to account for more recent acceleration data).

If a match is determined (212) to exist between the real-time acceleration data and one of the stored acceleration profiles, the mobile device can activate (215) an application that is associated with the matching acceleration profile. In this context, activating (215) an application can include launching the application if it is not already running in memory of the mobile device (e.g., as either a foreground, or active, application, or as background application that does not currently have input/output device focus). Activating (215) an application can also include changing the status of an already running application from a background application to a foreground applications. In some implementations, a change in status from a background application to a foreground application can include, for example, displaying any user interface associated with the application in a top layer of a display screen included in the mobile device, or giving the application active focus, such that it receives input from appropriate input devices and provides output to appropriate output devices.

In some implementations, activating (215) an application can further include configuring the state of the application. For example, if the activated application is a media player application, activating (215) the media player application can include launching it (e.g., starting it in memory), and beginning to play default media. As another example, if the activated application is a browser application program, activating (215) the browser application can include automatically accessing certain network-accessible information and displaying that information with the browser application. More particularly, for example, activating a browser can include activating three browser windows and accessing (e.g., retrieving) and displaying in one browser window international news information from one network-accessible site (e.g., from www.cnn.com), in another browser, local news information (e.g., from www.kare11.com), and in a third browser window, financial information (e.g., from online.barrons.com).

In some implementations, the method 201 may be periodically executed. That is, a comparison between real-time acceleration data (e.g., data stored in a portion of a circular buffer, such as a portion that stores most recent real-time acceleration data) and acceleration profiles may be made (212) every five seconds, ten seconds, 30 seconds, two minutes, or at some other interval. By frequently executing the method 201, the mobile device can respond quickly to changes in activity by the user. For example, with reference to the above jogging example, if the method 201 is executed every five seconds, a user may be more likely to enjoy media played by the media player application within a very short time of starting to jog. Thus, a short period can facilitate a fast response time for activating applications in response to current real-time acceleration data.

In some implementations, the mobile device employs a longer period for comparing (212) real-time acceleration data and acceleration profiles. A longer period can be advantageous in some situations since it can provide some amount of "hysteresis" in activating and deactivating applications. That is, in the context of the jogging example, a longer period may prevent the mobile device from deactivating the media player application if the user stops jogging for a minute. Moreover, a longer period may allow more real-time acceleration data to be used in the comparison (212) to stored acceleration profiles, which may increase the matching accuracy. In particular, for example, the mobile device may better distinguish similar stored acceleration profiles (e.g., jogging and walking profiles, train and vehicle profiles, etc.) if more real-time acceleration data is used (and a longer corresponding period, in some implementations). In addition, some profiles may be best characterized by a longer period of data than other acceleration profiles. For example, more data (e.g., data corresponding to a longer period of time) may be required to accurately characterize travel in start-and-stop traffic than to characterize jogging.

Figure 1J:
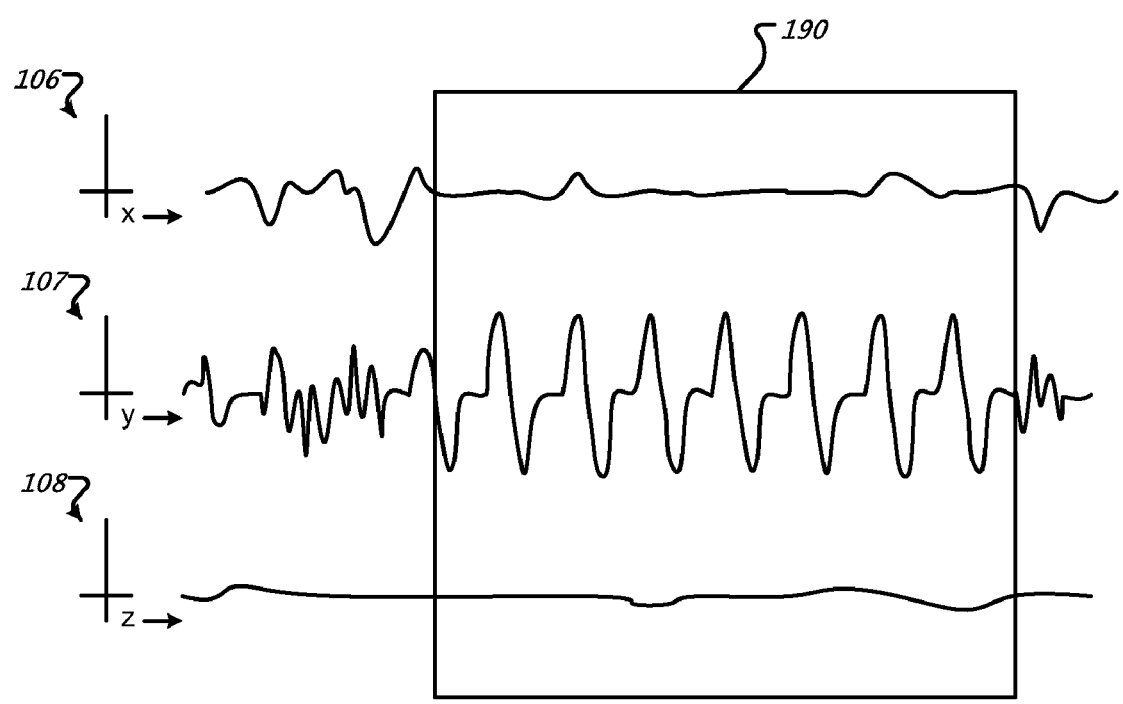
FIG. 1J illustrates an example window of acceleration data that can be identified and further processed.

In some implementations, raw acceleration data (e.g., real-time data captured by the mobile device for comparison to stored acceleration profiles) can be transformed in a manner that allows it to be more easily classified or characterized as corresponding to particular kind of activity than the raw data itself. For example, in some implementations, a time-ordered sequence of raw acceleration data can be initially analyzed or filtered to identify a portion of the sequence having a relatively consistent and periodic nature (e.g., given that many acceleration profiles that are associated with activities of interest have some periodic component). The identified portion, or window, can be analyzed further (e.g., transformed to a signature as described below), and the other portions of the time-ordered sequence can be ignored. In particular, with reference to FIG. 1J, a window 190 can be identified. In some implementations, the mobile device can identify the window 190 by analyzing frequency content of different portions the raw acceleration data (e.g., with a transform algorithm, such as a Discrete Fast Fourier Transform (DFFT); those portions may be identified as being included in the window that have a relatively small number of consistent frequency components relative to other portions of the raw acceleration data. In other implementations, statistical analysis may be applied to the raw acceleration data. In other implementations, as described briefly above, derivatives of the data can be employed or further processed, and multi-axis data may be transformed or translated to a different set of coordinates (e.g., to remove effects of positional orientation of the mobile device). In general, various techniques can be applied to identify relevant portions of acceleration data.

Once an appropriate portion of raw acceleration data has been identified, the raw acceleration data may be transformed to a signature or profile that may be more easily compared with other stored profiles. In some implementations, a signature or profile is generated through manipulation of the raw data in some manner For example, a signature can be generated by applying a mathematical algorithm or transform to a sequence of x-axis, y-axis and z-axis acceleration force values. The mathematical algorithm may, in practice, compress the data and highlight distinguishing features in the data. As a more specific example, a transform algorithm may be applied to the data (e.g., data such as that depicted in FIG. 1A or 1B) to identify a dominant frequency and average amplitude of the data along the y-axis 107. For data that is very periodic, the signature may include an average amplitude and dominant frequency along each axis.

To further facilitate subsequent analysis of signatures, certain aspects of either a stored profile or a real-time acceleration profile may also be normalized or otherwise processed. For example, given that different users have different step frequencies when running or walking, frequency content of acceleration data that corresponds to the user's step frequency may be normalized from, for example, a range of 1.3-2.7 Hz (75-160 steps/minute—a walking pace for many users) to 2.1 Hz (125 steps/minute); similarly, frequency content that corresponds to the user's step frequency may be normalized from, for example, a range of 2.7-3.3 Hz (160-200 steps/minute—a running pace for many users) to 3.0 Hz (180 steps/minute).

Amplitude data may also be normalized, for example, to a first value if a frequency component suggests walking, and to another higher amplitude value if a frequency component suggests running. As another example of processing, acceleration data can be "windowed" to exclude irrelevant data for the particular profile (e.g., as described above with reference to FIG. 1J). For example, user movement prior to the start of jogging can include stretching and placement of the mobile computing device in a pocket or strapping it to an arm. These movements can be identified and excluded, or filtered out of the acceleration profile representative of a user running. In another example, the profile for an automobile traveling at highway speeds may be windowed to exclude movement associated with the user getting into and starting the automobile.

Normalized acceleration profiles or signatures that are generated from real-time acceleration data can be compared to stored acceleration profiles in various ways. For example, many algorithms and systems exist for comparing images to each other (e.g., for purposes of classification or object recognition), or for comparing audio content to reference content (e.g., for purposes of verifying the source or detecting copying). The reader will appreciate that similar algorithms and systems (or other appropriate algorithms or systems) can be applied to classifying and comparing acceleration profiles or signatures. In some implementations, acceleration data may be stored in profiles in a digitized format. Normalized acceleration profiles or signatures that are generated from real-time acceleration data can also be digitized. The digitized files can be compared to determine a close match.

In some implementations, the acceleration profiles stored on the mobile device and the real-time acceleration data can be normalized or processed in the same way manner, in order to facilitate comparison of the real-time data to stored profiles.

Figure 2B:
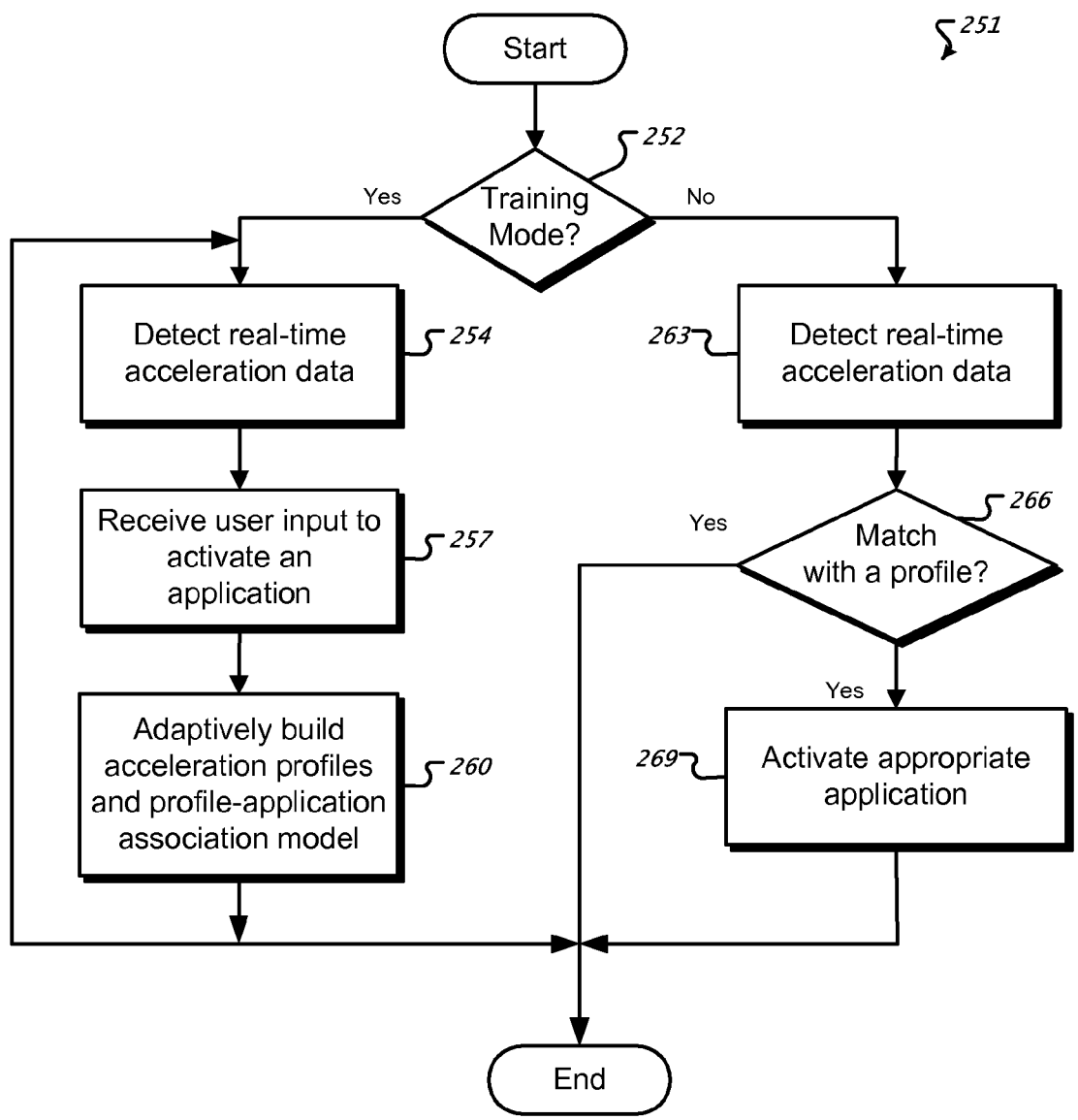
FIG. 2B illustrates an example method of adaptively training a mobile device to associate applications with acceleration profiles.

FIG. 2B illustrates an example method 251 of adaptively training a mobile device to associate application activations with acceleration profiles, which the mobile device may themselves build. FIG. 2B is described in greater detail below, after additional description is provided regarding adaptive training.

Figure 3A:
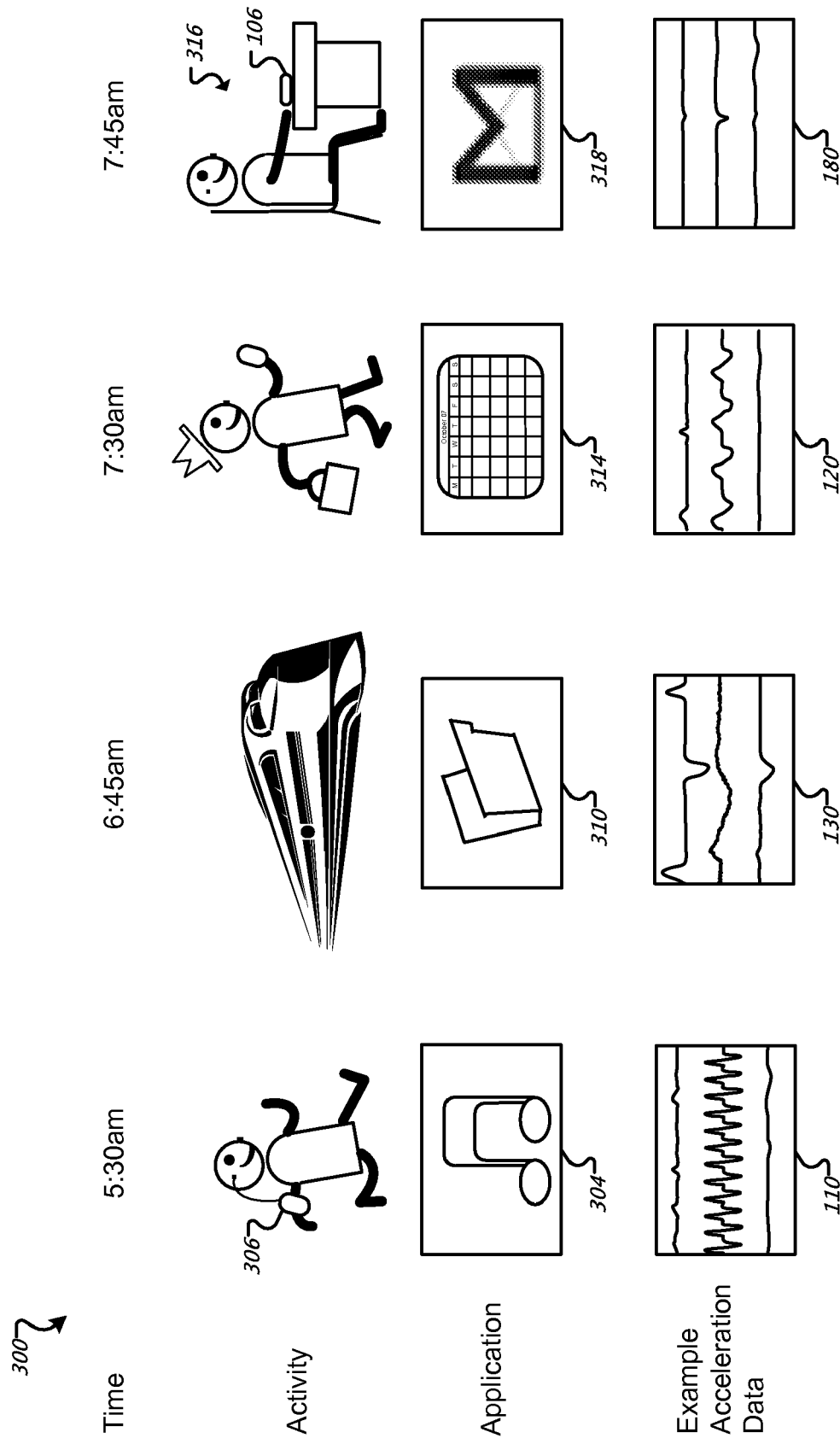
FIG. 3A is a diagram depicting a sequence of example activities that a user of a mobile computing device may engage in, and corresponding mobile device applications that the user may run while engaging in the activities.
Figure 3B:
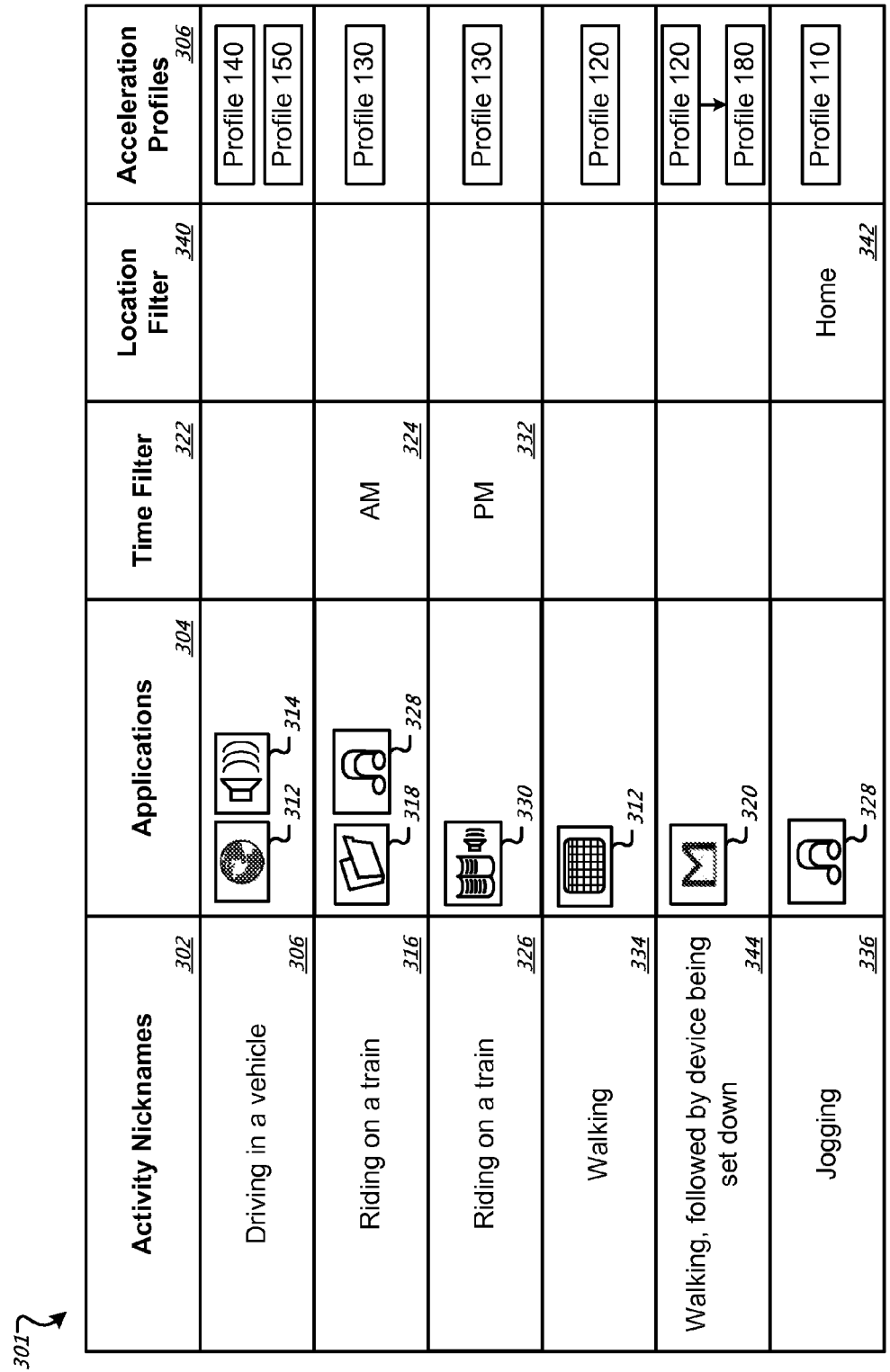
FIG. 3B illustrates an example user interface that can be used to associate various user activities (and corresponding acceleration profiles) with mobile device applications.
Figure 3B:
Figure 3B:
Figure 3B:
Figure 3B:
Figure 3B:
Figure 3B:
Figure 3B:

Turning to FIGS. 3A and 3B, a series of example activities, applications and corresponding acceleration profiles are now illustrated and described (FIG. 3A), as well as an example user interface for associating certain applications with certain activities (FIG. 3B).

FIG. 3A is a diagram 200 depicting a sequence of example activities that a user of a mobile computing device (e.g., a smartphone, PDA, cell phone, etc.) may engage in throughout the day, and corresponding applications that the user may run while engaging in the activities. In an example, as shown in FIG. 2, a user may regularly jog in the morning. While jogging, the user may employ a media player application 304 on his or her mobile device 306 to listen to music. While the user is jogging, the user's mobile device may capture the acceleration profile 110 (described above with reference to FIG. 1A).

Later in the morning, the user may ride a train to his or her office. While riding on the train, the user may regularly employ a browser application 310 to check stock prices, obtain a weather report for the day, and read current news from one or more network-accessible sites (e.g., www.msbnc.com, www.nytimes.com, news.google.com, online.barrons.com, etc.). While the user is riding the train, the user's mobile device may capture the acceleration profile 130 (described above with reference to FIG. 1C).

After getting off the train, the user may walk from the train station to his or her office. While the user is walking, the user may employ a calendar application 314 to check a calendar to view appointments and other activities that are scheduled for the day. While the user is walking, the user's mobile device may capture the acceleration profile 120 (described above with reference to FIG. 1B).

Once at the office, the user may sit down at a desk 316, set the mobile device on the desk and begin a work day by employing a messaging application 318 to check electronic messages (e.g., email messages, text messages, etc.). When the user sets the mobile device on the desk 316, the mobile device may capture the acceleration profile 180 (described above with reference to FIG. 1H).

FIG. 3B illustrates an example user interface 301 that can be used to associate various user activities (and corresponding acceleration profiles) with mobile device applications. As shown in one implementation, the user interface 301 can relate activities (e.g., by activity nicknames 302), applications 304, acceleration profiles 306, and, optionally (as shown), filter settings (e.g., time-based filter settings 322 and location-based filter settings 340), which can be used in associating activities 302 with applications 304 (or more particularly, acceleration profiles 306 corresponding to the activities 302 with the applications 304). Several specific groupings of applications 304 and acceleration profiles 306 are now described.

In some implementations, the user interface 301 enables users to drag and drop icons onto various portions of the interface to create associations. In particular, for example, graphical icons can be associated with different applications (e.g., a maps application 312, a browser application 318, a media player application, etc.). Acceleration profiles may also be dragged (e.g., from a library of icons associated with acceleration profiles, including "Profile 140," which may represent the acceleration profile 140 shown in FIG. 1D, and "Profile 150," which may represent the acceleration profile 150 shown in FIG. 1E) and dropped onto an appropriate place in the user interface 301.

Other information can be entered in the user interface in other ways. For example, activity nicknames 302 and filter information 322 and 340 may be entered in text-entry boxes (text-entry boxes not explicitly shown). As another example, time-filter information 322 may be entered through the use of drop-down boxes or menus (drop-down boxes or menus not shown). In general, the reader will appreciate that data can be entered in any appropriate manner; the user interface 301 is merely exemplary.

As depicted, a user of the mobile device can employ the user interface 301 to associate an acceleration profile to an application. In some cases, more than one acceleration profile can be associated with an application. In particular, for example, "Profile 140" (e.g., an acceleration profile corresponding to a mobile device in a vehicle in heavy, start-and-stop traffic) and "Profile 150" (e.g., an acceleration profile corresponding to a mobile device in smooth-flowing traffic traveling at highway speeds) may both be associated with a maps application 312. That is, if vehicle travel is detected—either vehicle travel in stop-and-go traffic or vehicle travel at highway speeds—a maps application 312 may be launched.

In some implementations, device settings can also be configured in response to acceleration profiles. For example, if real-time acceleration data matches either "Profile 140" or "Profile 150" (i.e., start-and-stop or highway travel), the mobile device may be switched to a speaker mode (e.g., depicted by setting 314). That is, applications that produce audio output may be switched to a mode where the audio output is provided through a speaker (e.g., rather than through, for example, a wired or BLUETOOTH headset connection).

In some implementations, multiple applications can be associated with an acceleration profile. As shown in one example, a browser application 318, a media player application 328 and an audio book application 330 may all be associated with "Profile 130" (e.g., an acceleration profile corresponding to a mobile device on a train). In some cases, multiple applications may be activated (e.g., the browser application 318 and the media player application 328). In some cases, only one of multiple applications may be automatically activated, and which application is automatically activated may be based on a filter setting 322.

Two examples of filtering are provided—time-based filtering, and location-based filtering. The reader will appreciate, however, that various other methods of filtering can be applied, such as, for example, filtering based on a day of the week, a month, a corporate quarter, a year, etc. Turning to time-based filtering, detection of travel on a train may selectively launch applications based on time-filter settings 324 and 332. In particular, in the example, shown, the browser and media player applications 318 and 328 can be activated in the morning in response to real-time acceleration data corresponding to travel by train (e.g., when the user is on his or her way into work); in the afternoon or evening (e.g., when the user is on his or way home, from work), the audio book application 330 can be activated in response to detection of real-time acceleration data corresponding to travel by train. In the above examples, time-based filtering is applied based on a distinction between AM and PM; in some implementations, time-based filtering may be based on proximity to two different times that are separated by at least a predetermined threshold (e.g., one hour, two hours, four hours, eight hours, etc.).

Other kinds of filtering can be provided for. For example, GPS functionality in the mobile device may enable location-based filtering. Detection of real-time acceleration data corresponding to jogging (e.g., profile 110) may cause the media player application 328 to be activated—but only if the mobile device is near "Home" (e.g., as determined by current GPS-based location information (or other forms of location information) and a "Home" setting that can be configured (e.g., using another interface, which is not shown)). In the context of this example, the mobile device can activate the media player application when the user is going for a regular jog near his or her home, but the media player may not be activated when the user is engaged in a similar activity (e.g., jogging or running) in a different context (e.g., when the user is sprinting down a street near his or her office in order to catch a train).

Figure 3C:
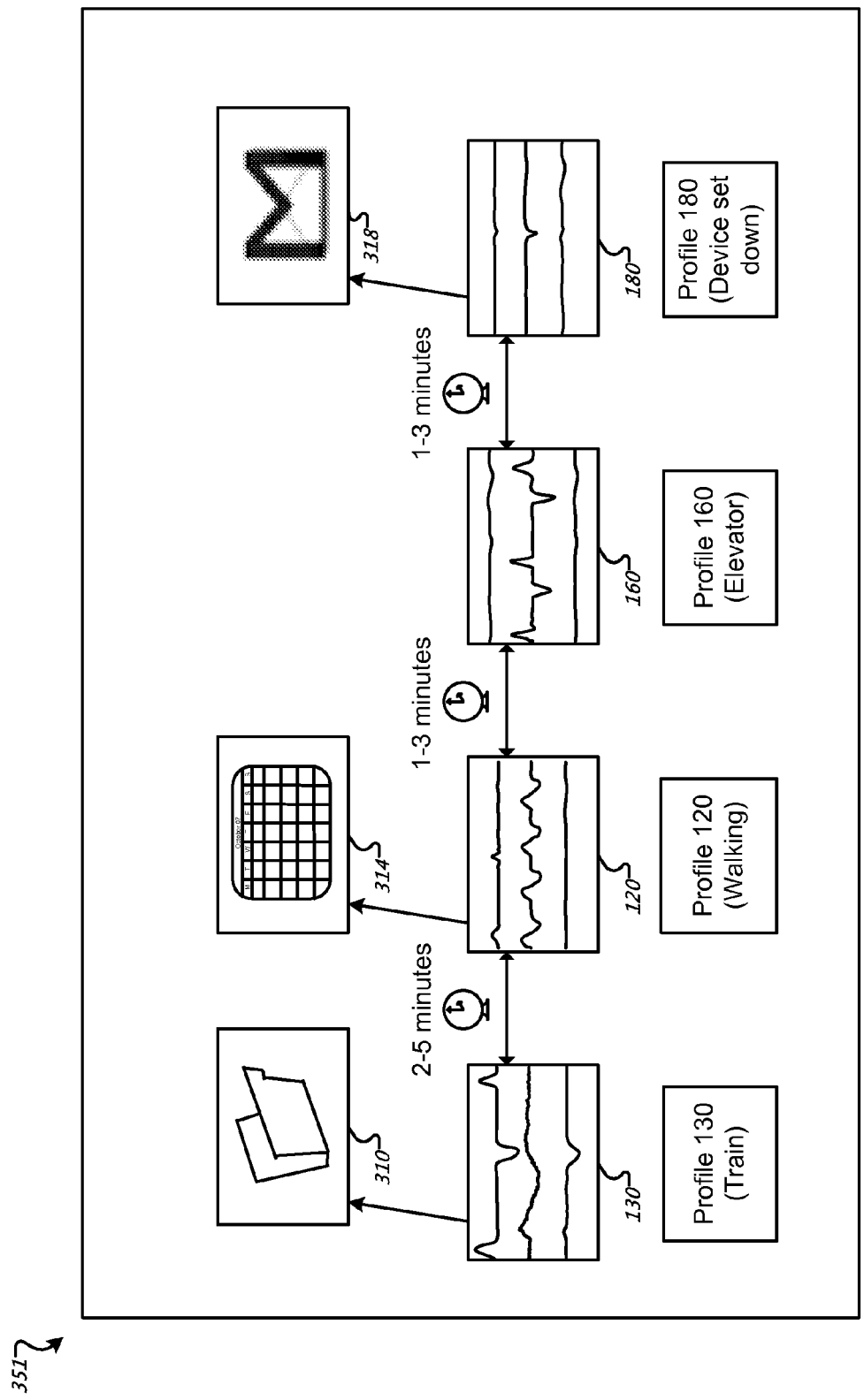
FIG. 3C illustrates one example user interface that can be employed to configure the mobile device to activate various applications in response to a sequence of activities.

In some implementations, an application can be launched based on a sequence of activities (and a sequence of matches of real-time acceleration data to acceleration profiles). FIG. 3C illustrates one example user interface 351 that can be employed to configure the mobile device to launch various applications in response to a sequence of activities. In this example, the user may populate the user interface 351 by dragging and dropping appropriate icons in a sequence, and, optionally specifying a time between activities.

Acceleration data is graphically depicted in the user interface 351, but this graphical depiction may be omitted, and the user interface 351 may be configured based only on labeled acceleration profile icons, application icons, time-delay icons, and various connectors (e.g., two-headed arrows to indicate sequence; single-headed arrows to indicate an effect (arrow end) in response to a cause (end opposite the arrow).

As shown in one example, real-time detection of an acceleration profile 130 associated with a train can cause a browser application 310 to be launched. Real-time detection of an acceleration profile 120 associated with walking, approximately 2-5 minutes after real-time acceleration data that matches the train profile 130 is detected, can cause a calendar application to be launched 314. Real-time detection of an acceleration profile 160 associated with an elevator, approximately 1-3 minutes after real-time acceleration data that matches the walking profile 120 is detected, followed 1-3 minutes later by detection of real-time acceleration data that matches a profile corresponding to the mobile device being set down, can cause the messaging application 318 to be activated.

In some implementations, applications are only launched if the current real-time acceleration data matches an appropriate profile and if previous real-time acceleration data matched another appropriate profile. That is, in some implementations, the mobile device can improve recognition accuracy by identifying real-time acceleration data that matches a time-ordered sequence of acceleration profiles. In particular, for example, the calendar application 314 may not be automatically launched when real-time acceleration data that matches the walking profile 120 is detected in isolation (i.e., not 2-5 minutes after real-time acceleration data that matches the train profile 130). Similarly, the messaging application 318 may not be automatically launched unless real-time acceleration data is detected that matches the example, sequence.

The user interfaces 301 and 351 is merely exemplary. In general a user interface for configuring associations between activities and their corresponding acceleration profiles and activating applications can take any form. In some implementations, the user interface 301 is provided through several different interfaces. In some implementations, the user interface 301 is provided on the mobile device itself; in other implementations, the user 301 interface is provided through a configuration tool external to the mobile device (e.g., in a computer-based or web-based application)—in which case, configuration settings can be transferred to the mobile device in any appropriate manner. Many other variations are contemplated.

In some implementations, as described in more detail below, a mobile computing device may be adaptively trained to "learn" a user's schedule in an automated manner. The user interface 301 may be filled in as appropriate as the mobile device adaptively learns a user's habits and activities (or corresponding configuration settings may be stored, without populating the user interface 301). The user interface 301 can also be made available to the user during the training process. For example, the user may accelerate the training process by filling in areas of the user interface 300 that are not populated at a particular point in time. Alternatively, the user may employ the user interface 301 to override the trained settings.

To adaptively train, the mobile device may provide a training mode and an operating mode. In the training mode, the mobile device can monitor both real-time acceleration data and the user's activation of various applications. Over time, the mobile device can make and strengthen correlations between real-time acceleration data and the activating (or deactivating) of certain applications. In an operating mode, the mobile device can monitor real-time acceleration data and apply the previously made correlations to activate appropriate applications. These processes are illustrated and described in more detail with reference to FIGS. 4A and 4B.

Figure 4A:
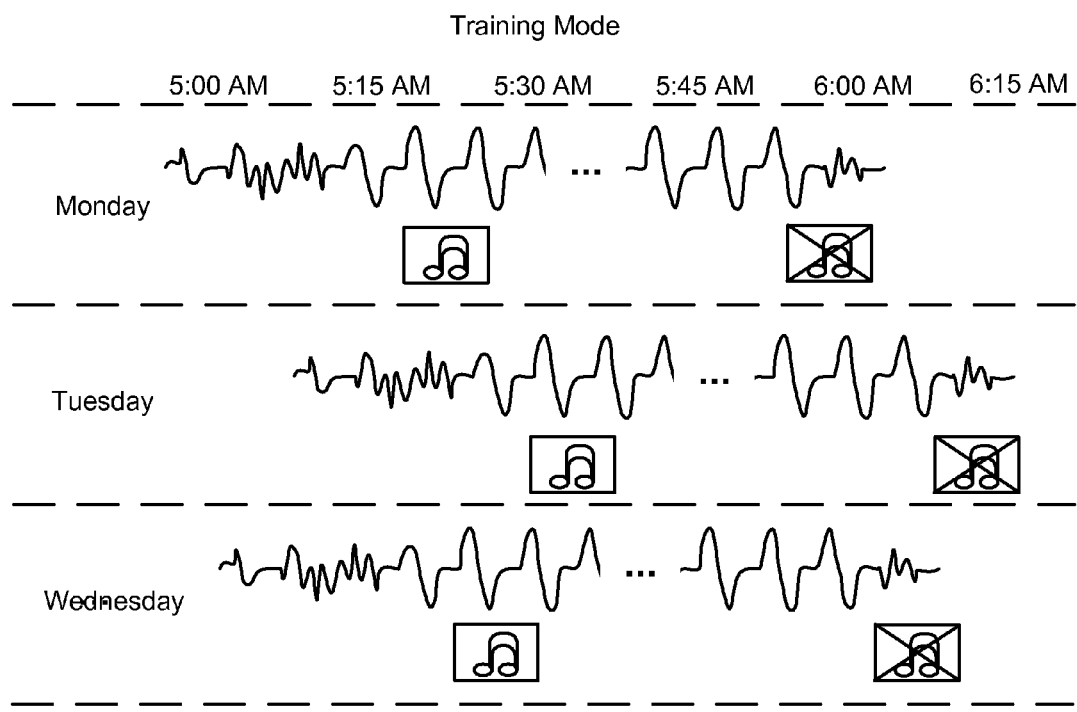
FIGS. 4A and 4B depict, respectively, an example training mode, in which a mobile device can adaptively correlate the activating of applications with real-time acceleration data, and a corresponding operating mode.
Figure 4B:
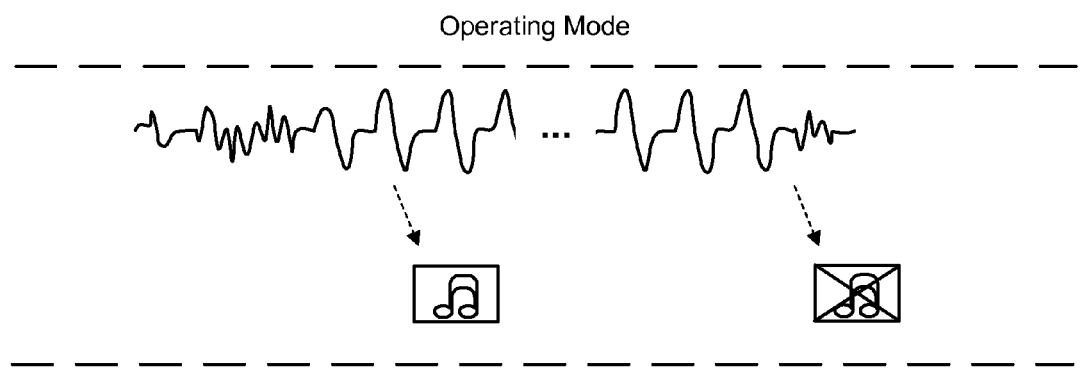

FIGS. 4A and 4B depict, respectively, an example training mode, in which a mobile device can adaptively correlate the activating of applications with real-time acceleration data, and a corresponding operating mode. For purposes of illustration, the example depicts real-time acceleration data corresponding to a user jogging each of three mornings, and activating a media player application while jogging. As depicted in one example, the user begins jogging on Monday at about 5:15 AM and almost immediately activates a media player application. The user stops jogging close to 6:00 AM and almost immediately stops the media player application.

To adaptively train, the mobile device may analyze real-time acceleration data both before and after an application is activated or deactivated (e.g., for a predetermined time before and after, such as five seconds, 30 seconds, one minute, two minutes, etc.). Thus, after the first day in training mode, the mobile device may associate activation of the media player application with random acceleration data before the activation (e.g., acceleration data associated with the user getting ready to jog), and periodic acceleration data having certain frequency and amplitude content following the activation (e.g., acceleration data associated with jogging). Similarly, the mobile device may associate deactivation of the media player activation with periodic acceleration data having certain frequency and amplitude content before the deactivation and random acceleration data following the deactivation. The activation and deactivation may further be associated with a time (e.g., a specific time, such as 5:15 AM and 6:00 AM, or a time range, such as 5:00-5:30 AM and 5:45-6:15 AM) or a general location (e.g., based on GPS information, which is not depicted in FIGS. 4A and 4B).

After the second and third days (e.g., Tuesday and Wednesday) of detecting similar real-time acceleration data and a similar relationship between the detected real-time acceleration data and the activating and deactivating of the media player application (and a generally similar relationship to the real-time acceleration data, the application and the time of day), the mobile device may have adaptively configured itself. In particular, for example, the mobile device may have configured itself to activate a media player application immediately upon detecting real-time acceleration data having frequency and amplitude content similar to the frequency and amplitude content detected during the training mode (and associated with jogging); moreover, the mobile device may have configured itself to deactivate the media player application after the real-time acceleration data having the trained frequency and amplitude content is no longer detected.

FIG. 4B illustrates operation of the mobile device in an operating mode—for example, operation based on the adaptive training. As depicted by the dashed arrows, the media player application can be automatically activated upon detection of real-time periodic acceleration data (e.g., real-time acceleration data that matches a jogging profile) and automatically deactivated when the real-time periodic acceleration data is no longer detected.

In some implementations, a mobile device can adaptively learn relationships between sequences of acceleration data and multiple activations or deactivations of various mobile device applications (e.g., such as sequences like that depicted in FIG. 3C). For example, the mobile device could, over a training period, configure itself to detect a first acceleration profile at a general time of day (e.g., an acceleration profile corresponding to train travel), during which a first application is activated (e.g., a browser application); detect, after some period of time (e.g., a few minutes), a second acceleration profile (e.g., an acceleration profile corresponding to walking), during which a second application is activated (e.g., a calendar application); and detect, after another period of time (e.g., a few minutes), third and fourth acceleration profiles (e.g., acceleration profiles corresponding to riding an elevator and to the mobile device being set down on a hard surface), after which a third application is activated (e.g., an email application).

In the above example, real-time acceleration data in the period of time between the first and second acceleration profiles may be ignored. This data may be random in nature, or the data may have a regular character that is different than the real-time acceleration data before and after. In some implementations, the data corresponds to a user's transition from one activity to another. For example, the mobile device may detect real-time acceleration data that is consistent with riding a train, followed by random real-time acceleration data, followed by real-time acceleration that is consistent with walking. The random real-time acceleration data may correspond to a transition period during which the user is getting off a train and walking up or down steps, possibly in heavy crowds, before reaching a sidewalk, where the user may be able to walk normally (at which point the mobile device may detect consistent, periodic real-time acceleration consistent with walking).

A time associated with the period between acceleration profiles may be factored into the adaptively configured model. For example, the mobile device may adaptively determine that real-time acceleration data associated with a train, followed by three minutes of random real-time acceleration data, followed by real-time acceleration data associated with walking should cause a calendar application to be activated.

Any suitable method for adaptively training can be employed. That is, any suitable algorithm can be applied to determine correlations (e.g., training signatures) between acceleration data and the activation or deactivation of applications. Any suitable training period can also be used. For example, depending on the complexity of a user's schedule and habits, two weeks of training data may need to be collected in order for the mobile device to adaptively build an acceleration data-application model; in other cases, more or less time may be required (e.g., three days, three weeks, etc.).

In some implementations, the training process may progressively populate and refine a user interface, such as the user interface 301 shown in FIG. 3B. In such implementations, the user may expedite the training process by filling in or changing any information that is populated by the training process.

Once sufficient training has been completed, the user can switch his or her mobile device to an operating mode, in which the mobile device monitors real-time acceleration data, compares the real-time acceleration data to the various acceleration profiles on the mobile device, and activates appropriate applications based on the adaptively configured model.

In some implementations, a training mode can be used to refine or update an acceleration-application model. That is, after the user interface 301 has been populated (either manually by the user, automatically by a training algorithm, or by a combination of the two), the user of the mobile device can switch to a training mode (e.g., for a few days or a week or two) to automatically update the mobile device to detect a new pattern of activity (e.g., to refine an application-acceleration model).

In the above description, acceleration data is described by the activity it may represent, but the reader will appreciate that correlations may be automatically established between applications and acceleration data at the mobile device determining the activity that corresponds to a particular acceleration profile. That is, the mobile device may detect real-time acceleration data that is periodic in nature, has a particular frequency and amplitude and that is associated with activating a particular application (e.g., a media player application) without determining that the real-time acceleration data is associated with "jogging"). However, to facilitate manual changes to an application-acceleration model, a user may enter a label or activity nickname (or graphical icon) to different acceleration profiles. Similarly, pre-stored acceleration profiles or acceleration profiles that may be provided by third-parties may come pre-labeled or associated with descriptive graphical icons.

Turning back to FIG. 2B, adaptive training is further described. In particular, FIG. 2B illustrates an example method 251 of adaptively training a mobile device to adaptively build an application-acceleration model in a training model, then use the model in an operating mode to automatically activate applications in response to real-time acceleration data.

The method 251 can include determining (252) whether the mobile device is in a training mode or an operating mode. In some implementations, the mode is determined by user input. In particular, for example, a user can configure the mobile device to be in a training mode, in which case the mobile device detects (254) real-time acceleration data and monitors (257) manual application activations (as well as deactivations, in some cases), and adaptively builds (260) a model to correlate specific acceleration data with specific application activations. That is, over a period of a few days or weeks, the mobile device can apply a learning algorithm to learn correlations between specific patterns or sequences of acceleration data and specific application activations.

In some implementations, acceleration profiles are themselves adaptively built (260). That is, the mobile device may identify windows of like acceleration data (e.g., data having consistent, periodic characteristics, such as, for example, the window 190 of acceleration data depicted in FIG. 1J. Like acceleration data may be averaged during the training mode and stored as an acceleration profile. As described above, each acceleration profile may be normalized or processed in some other manner to facilitate subsequent comparison of real-time acceleration data with the profile.

If the mobile device is determined (252) to be in an operating mode, real-time acceleration data can be detected (263), and a comparison algorithm can be applied to the real-time acceleration data to determine (266) if a match exists between the real-time data and a stored profile. If a match is determined (266) to exist, an appropriate application can be activated (269) (or deactivated) based on the adaptively built (260) association model.

Figure 5:
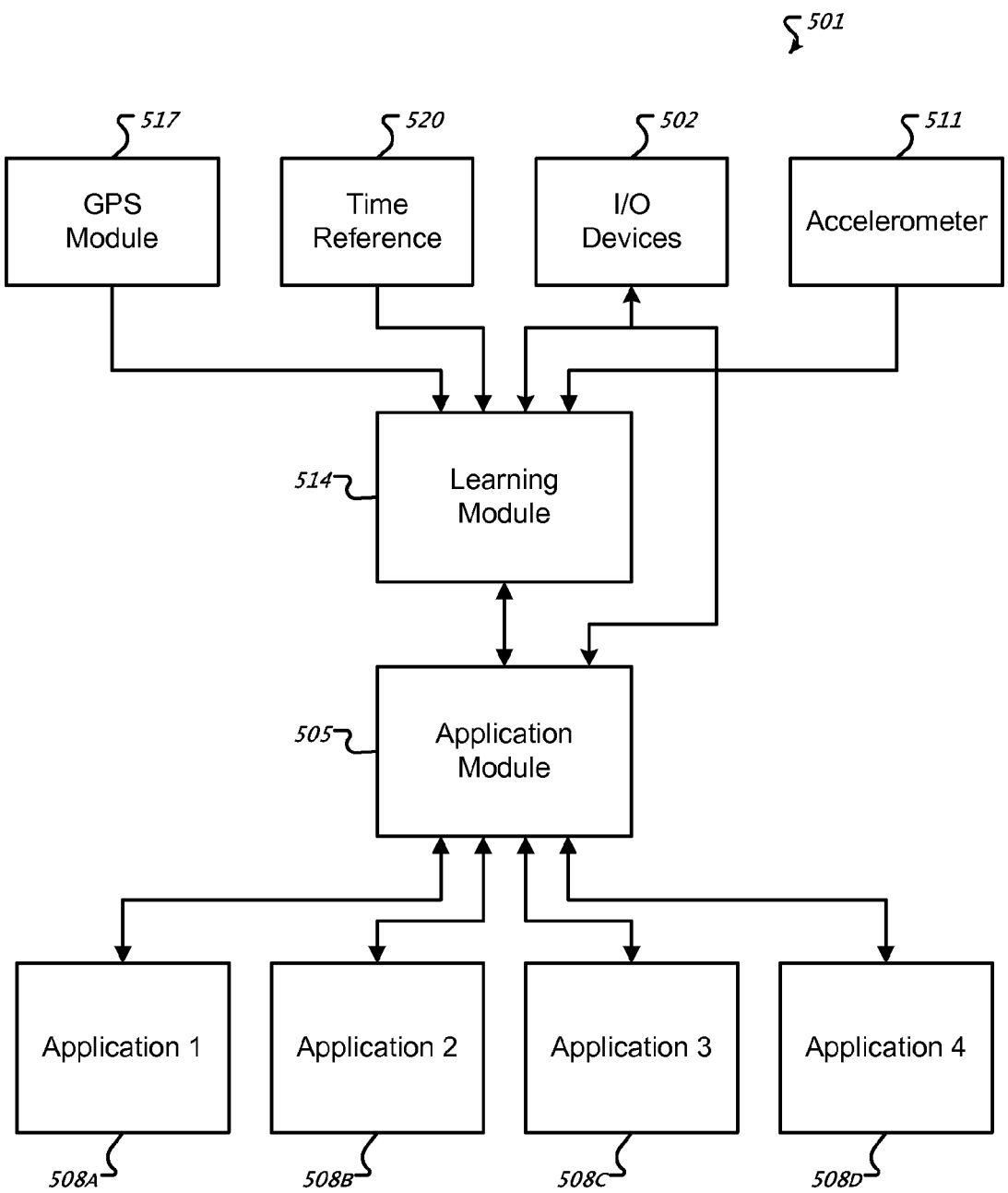
FIG. 5 is a block diagram of an example mobile device that can receive and process real-time acceleration data, correlate the processed real-time acceleration information with one or more acceleration profiles, and activate one or more applications based on the correlation.

In the description above, various operations are described that may be automated to one degree or another. For example, a device may be trained to learn a user's regular activities and correlate particular physical activities (e.g., based on acceleration data) with particular applications. Some implementations may be more interactive. For example, a device may prompt a user to confirm a detected match between acceleration data and an identified profile (e.g., a profile that is stored on the device; stored on a removable storage medium; accessible from a public, semi-private or private network-accessible location; etc.). As another example, the device may prompt a user to confirm the desired launch of an application or the desired configuration of the device In particular, for example, upon capturing acceleration data that is determined to match a jogging profile, the device may query the user regarding whether a media application should be launched, rather than automatically launching the application. In gen- FIG. 5 is a block diagram of an example mobile device 501 that can receive and process real-time acceleration data, correlate the processed acceleration information with one or more acceleration profiles, and activate one or more applications based on the correlation. Only a few aspects of the example mobile device 501 are described with reference to FIG. 5; other aspects are described with reference to FIGS. 6-10.

In one implementation as shown, the mobile device 501 includes I/O devices 502 (e.g., keyboard or buttons and display screen), which can interface to an application module 505 (e.g., a software-based operating system component or other component that manages applications). The application module 505 can control the activation and deactivation of various applications 508A, 508B, 508C and 508D. Active applications may provide various user functions by, for example, receiving input from the I/O devices 502, processing the received input (along with other data stored in memory (not shown) or accessible from a network-accessible source (not shown)), and providing output (e.g., graphical output) to be presented on an output device included in the I/O devices 502.

The mobile device 501 can also include an accelerometer 511 (or another source of real-time acceleration information). The accelerometer 511 can provide real-time acceleration data to a learning module 514, which can also receive user input to activate or deactivate the applications 508A-D. In some implementations, the learning module adaptively correlates, in a training mode, acceleration data and user input to activate applications based on contemporaneous acceleration data. In an operating mode, the learning module can activate applications based on real-time acceleration data and the adaptively built correlations. In some implementations, the learning module also builds acceleration profiles (e.g., identifies windows of acceleration data that should be included in a profile and adaptively builds (e.g., averages or refines over time) the acceleration profiles).

In some implementations, the learning module 514 can be replaced with a correlation module, which may store various acceleration profiles (e.g., profiles as depicted in FIGS. 1A-1H) and cause an application to be launched when real-time acceleration data received from the accelerometer 511 matches one of the stored acceleration profiles to which the application is associated.

In some implementations, the learning module 514 (or correlation module—not shown) can receive additional input from a GPS module 517 (or another component that acquires current location information of the mobile device 501) and from a time reference (e.g., an internal or network-accessible clock or other time signal). As described above, either or both of location information (e.g., information from the GPS module 517) and time information (e.g., from the time reference 520) can be used in adaptively building the correlations. For example, as described with reference to FIG. 3B, correlations may be time-filtered, location filtered, or filtered based on some other parameter.

Figure 6:
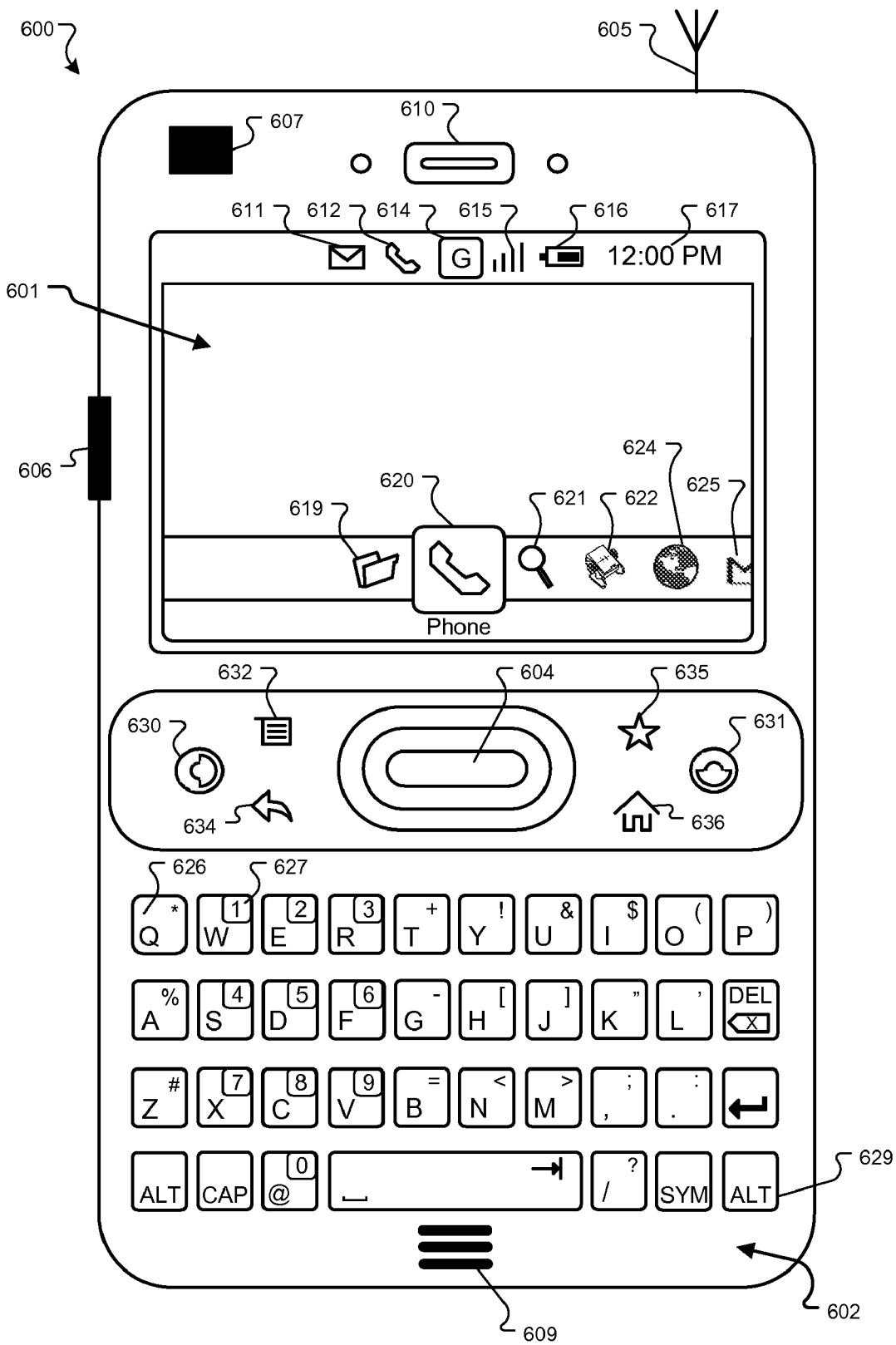
FIG. 6 is a schematic representation of an exemplary mobile device that can automatically activate applications based on real-time acceleration data.

Referring now to FIG. 6, the exterior appearance of an exemplary device 600 that facilitates automatic activation of applications in response to real-time acceleration data corresponding to the device 600 captured by the device 600 is illustrated. Briefly, and among other things, the device 600 includes a processor configured to analyze real-time acceleration data (e.g., provided by an accelerometer included in the device), compare the real-time acceleration data with acceleration profiles stored in the device 600 to identify a matching acceleration profile, and activate an application, if that application was previously associated with the matching acceleration profile.

In more detail, the hardware environment of the device 600 includes a display 601 for displaying text, images, and video to a user; a keyboard 602 for entering text data and user commands into the device 600; a pointing device 604 for pointing, selecting, and adjusting objects displayed on the display 601; an antenna 605; a network connection 606; a camera 607; a microphone 609; and a speaker 610. Although the device 600 shows an external antenna 605, the device 600 can include an internal antenna, which is not visible to the user.

The display 601 can display video, graphics, images, and text that make up the user interface for the software applications used by the device 600, and the operating system programs used to operate the device 600. Possible elements that may be displayed on the display 601 include, for example, a new mail indicator 611 that alerts a user to the presence of a new message; an active call indicator 612 that indicates that a telephone call is being received, placed, or is occurring; a data standard indicator 614 that indicates the data standard currently being used by the device 600 to transmit and receive data; a signal strength indicator 615 that indicates a measurement of the strength of a signal received by via the antenna 605, such as by using signal strength bars; a battery life indicator 616 that indicates a measurement of the remaining battery life; or a clock 617 that outputs the current time.

The display 601 may also show application icons representing various applications available to the user, such as a web browser application icon 619, a phone application icon 620, a search application icon 621, a contacts application icon 622, a mapping application icon 624, an email application icon 625, or other application icons. In one example implementation, the display 601 is a quarter video graphics array (QVGA) thin film transistor (TFT) liquid crystal display (LCD), capable of 16-bit color or better.

A user uses the keyboard (or "keypad") 602 to enter commands and data to operate and control the operating system and applications. The keyboard 602 includes standard keyboard buttons or keys associated with alphanumeric characters, such as keys 626 and 627 that are associated with the alphanumeric characters "Q" and "W" when selected alone, or are associated with the characters "*" and "1" when pressed in combination with key 629. A single key may also be associated with special characters or functions, including unlabeled functions, based upon the state of the operating system or applications invoked by the operating system. For example, when an application calls for the input of a numeric character, a selection of the key 627 alone may cause a "1" to be input.

In addition to keys traditionally associated with an alphanumeric keypad, the keyboard 602 also includes other special function keys, such as an establish-call key 630 that causes a received call to be answered or a new call to be originated; a terminate call key 631 that causes the termination of an active call; a drop down menu key 632 that causes a menu to appear within the display 601; a backward navigation key 634 that causes a previously accessed network address to be accessed again; a favorites key 635 that causes an active web page to be placed in a bookmarks folder of favorite sites, or causes a bookmarks folder to appear; a home page key 636 that causes an application invoked on the device 600 to navigate to a predetermined network address; or other keys that provide for multiple-way navigation, application selection, and power and volume control.

The user uses the pointing device 604 to select and adjust graphics and text objects displayed on the display 601 as part of the interaction with and control of the device 600 and the applications invoked on the device 600. The pointing device 604 is any appropriate type of pointing device, and may be a joystick, a trackball, a touch-pad, a camera, a voice input device, a touch screen device implemented in combination with the display 601, or any other input device.

The antenna 605, which can be an external antenna or an internal antenna, is a directional or omni-directional antenna used for the transmission and reception of radiofrequency (RF) signals that implement point-to-point radio communication, wireless local area network (LAN) communication, or location determination. The antenna 605 may facilitate point-to-point radio communication using the Specialized Mobile Radio (SMR), cellular, or Personal Communication Service (PCS) frequency bands, and may implement the transmission of data using any number or data standards. For example, the antenna 605 may allow data to be transmitted between the device 600 and a base station using technologies such as Wireless Broadband (WiBro), Worldwide Interoperability for Microwave ACCess (WiMAX), 3GPP Long Term Evolution (LTE), Ultra Mobile Broadband (UMB), High Performance Radio Metropolitan Network (HIPERMAN), iBurst or High Capacity Spatial Division Multiple Access (HC-SDMA), High Speed OFDM Packet Access (HSOPA), High-Speed Packet Access (HSPA), HSPA Evolution, HSPA+, High Speed Upload Packet Access (HSUPA), High Speed Downlink Packet Access (HSDPA), Generic Access Network (GAN), Time Division-Synchronous Code Division Multiple Access (TD-SCDMA), Evolution-Data Optimized (or Evolution-Data Only)(EVDO), Time Division-Code Division Multiple Access (TD-CDMA), Freedom Of Mobile Media Access (FOMA), Universal Mobile Telecommunications System (UMTS), Wideband Code Division Multiple Access (W-CDMA), Enhanced Data rates for GSM Evolution (EDGE), Enhanced GPRS (EGPRS), Code Division Multiple Access-2000 (CDMA2000), Wideband Integrated Dispatch Enhanced Network (WiDEN), High-Speed Circuit-Switched Data (HSCSD), General Packet Radio Service (GPRS), Personal Handy-Phone System (PHS), Circuit Switched Data (CSD), Personal Digital Cellular (PDC), CDMAone, Digital Advanced Mobile Phone System (D-AMPS), Integrated Digital Enhanced Network (IDEN), Global System for Mobile communications (GSM), DataTAC, Mobitex, Cellular Digital Packet Data (CDPD), Hicap, Advanced Mobile Phone System (AMPS), Nordic Mobile Phone (NMP), Autoradiopuhelin (ARP), Autotel or Public Automated Land Mobile (PALM), Mobiltelefonisystem D (MTD), Offentlig Landmobil Telefoni (OLT), Advanced Mobile Telephone System (AMTS), Improved Mobile Telephone Service (IMTS), Mobile Telephone System (MTS), Push-To-Talk (PTT), or other technologies. Communication via W-CDMA, HSUPA, GSM, GPRS, and EDGE networks may occur, for example, using a QUALCOMM MSM7200A chipset with an QUALCOMM RTR6285™ transceiver and PM7540™ power management circuit.

The wireless or wired computer network connection 606 may be a modem connection, a local-area network (LAN) connection including the Ethernet, or a broadband wide-area network (WAN) connection such as a digital subscriber line (DSL), cable high-speed internet connection, dial-up connection, T-1 line, T-3 line, fiber optic connection, or satellite connection. The network connection 606 may connect to a LAN network, a corporate or government WAN network, the Internet, a telephone network, or other network. The network connection 606 uses a wired or wireless connector. Example wireless connectors include, for example, an INFRARED DATA ASSOCIATION (IrDA) wireless connector, a Wi-Fi wireless connector, an optical wireless connector, an INSTITUTE OF ELECTRICAL AND ELECTRONICS ENGINEERS (IEEE) Standard 802.11 wireless connector, a BLUETOOTH wireless connector (such as a BLUETOOTH version 1.2 or 3.0 connector), a near field communications (NFC) connector, an orthogonal frequency division multiplexing (OFDM) ultra wide band (UWB) wireless connector, a time-modulated ultra wide band (TM-UWB) wireless connector, or other wireless connector. Example wired connectors include, for example, a IEEE-1394 FIREWIRE connector, a Universal Serial Bus (USB) connector (including a mini-B USB interface connector), a serial port connector, a parallel port connector, or other wired connector. In another implementation, the functions of the network connection 606 and the antenna 605 are integrated into a single component.

The camera 607 allows the device 600 to capture digital images, and may be a scanner, a digital still camera, a digital video camera, other digital input device. In one example implementation, the camera 607 is a 3 mega-pixel (MP) camera that utilizes a complementary metal-oxide semiconductor (CMOS).

The microphone 609 allows the device 600 to capture sound, and may be an omni-directional microphone, a unidirectional microphone, a bi-directional microphone, a shotgun microphone, or other type of apparatus that converts sound to an electrical signal. The microphone 609 may be used to capture sound generated by a user, for example when the user is speaking to another user during a telephone call via the device 600.

The speaker 610 allows the device to convert an electrical signal into sound, such as a voice from another user generated by a telephone application program, or a ring tone generated from a ring tone application program. Furthermore, although the device 600 is illustrated in FIG. 6 as a handheld device, in further implementations the device 600 may be a laptop, a workstation, a midrange computer, a mainframe, an embedded system, telephone, desktop PC, a tablet computer, a PDA, or other type of computing device.

Figure 7:
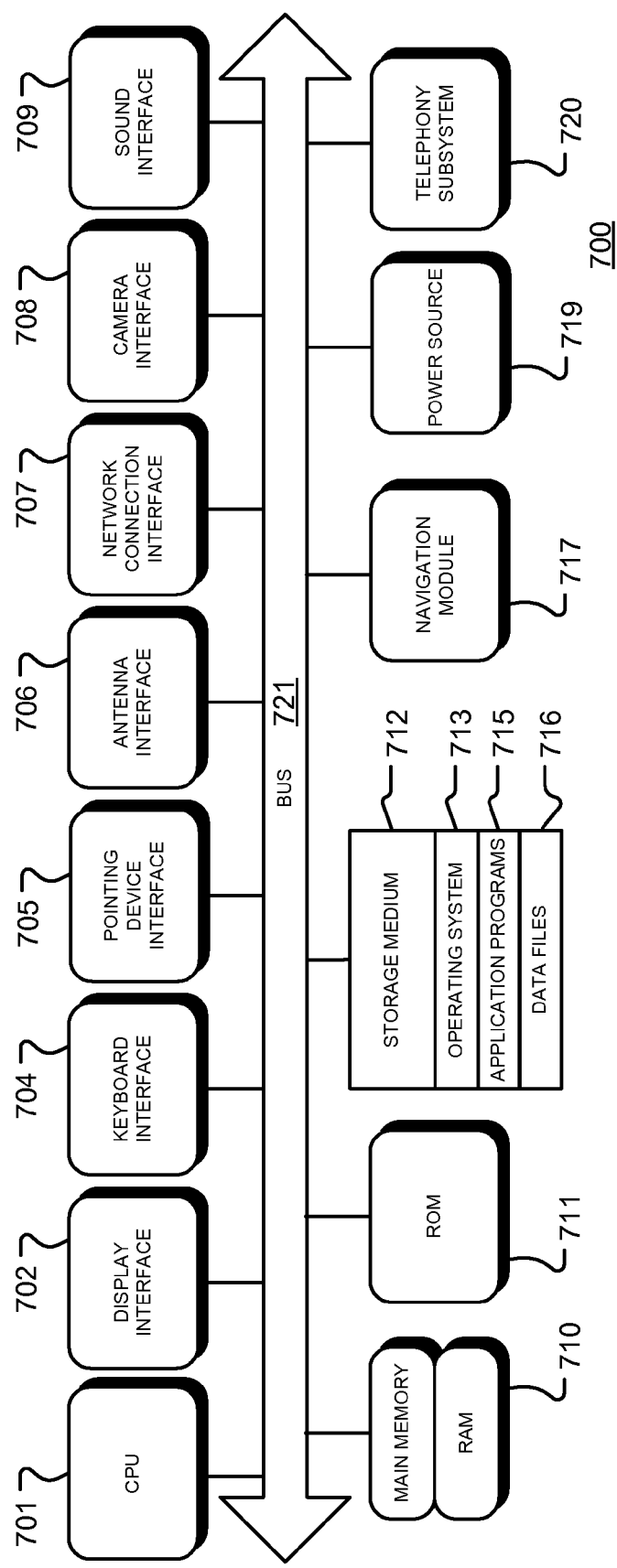
FIG. 7 is a block diagram illustrating additional details of the internal architecture of the device of FIG. 6.

FIG. 7 is a block diagram illustrating an internal architecture 700 of the device 600. The architecture includes a central processing unit (CPU) 701 where the computer instructions that comprise an operating system or an application are processed; a display interface 702 that provides a communication interface and processing functions for rendering video, graphics, images, and texts on the display 601, provides a set of built-in controls (such as buttons, text and lists), and supports diverse screen sizes; a keyboard interface 704 that provides a communication interface to the keyboard 602; a pointing device interface 705 that provides a communication interface to the pointing device 604; an antenna interface 706 that provides a communication interface to the antenna 605; a network connection interface 707 that provides a communication interface to a network over the computer network connection 606; a camera interface 708 that provides a communication interface and processing functions for capturing digital images from the camera 607; a sound interface 709 that provides a communication interface for converting sound into electrical signals using the microphone 609 and for converting electrical signals into sound using the speaker 610; a random access memory (RAM) 710 where computer instructions and data are stored in a volatile memory device for processing by the CPU 701; a read-only memory (ROM) 711 where invariant low-level systems code or data for basic system functions such as basic input and output (I/O), startup, or reception of keystrokes from the keyboard 602 are stored in a non-volatile memory device; a storage medium 712 or other suitable type of memory (e.g. such as RAM, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives), where the files that comprise an operating system 713, application programs 715 (including, for example, a web browser application, a widget or gadget engine, and or other applications, as necessary, and further including applications for analyzing real-time acceleration data, comparing the real-time acceleration data to stored acceleration profiles to identify matching acceleration profiles, launching applications that are associated with the matching acceleration profiles and adaptively building acceleration profiles and learning correlations between acceleration data and activation of various applications) and data files 716 are stored; a navigation module 717 that provides a real-world or relative position or geographic location of the device 600; a power source 719 that provides an appropriate alternating current (AC) or direct current (DC) to power components; and a telephony subsystem 720 that allows the device 600 to transmit and receive sound over a telephone network. The constituent devices and the CPU 701 communicate with each other over a bus 721.

The CPU 701 can be one of a number of computer processors. In one arrangement, the computer CPU 701 is more than one processing unit. The RAM 710 interfaces with the computer bus 721 so as to provide quick RAM storage to the CPU 701 during the execution of software programs such as the operating system application programs, and device drivers. More specifically, the CPU 701 loads computer-executable process steps from the storage medium 712 or other media into a field of the RAM 710 in order to execute software programs. Data is stored in the RAM 710, where the data is accessed by the computer CPU 701 during execution. In one example configuration, the device 600 includes at least 128 MB of RAM, and 256 MB of flash memory.

The storage medium 712 itself may include a number of physical drive units, such as a redundant array of independent disks (RAID), a floppy disk drive, a flash memory, a USB flash drive, an external hard disk drive, thumb drive, pen drive, key drive, a High-Density Digital Versatile Disc (HD-DVD) optical disc drive, an internal hard disk drive, a Blu-Ray optical disc drive, or a Holographic Digital Data Storage (HDDS) optical disc drive, an external mini-dual in-line memory module (DIMM) synchronous dynamic random access memory (SDRAM), or an external micro-DIMM SDRAM. Such computer readable storage media allow the device 600 to access computer-executable process steps, application programs and the like, stored on removable and non-removable memory media, to off-load data from the device 600, or to upload data onto the device 600.

A computer program product is tangibly embodied in storage medium 712, a machine-readable storage medium. The computer program product includes instructions that, when read by a machine, operate to cause a data processing apparatus to store image data in the mobile device. In some implementations, the computer program product includes instructions that process acceleration data, adaptively build acceleration data-application correlations, activate applications in response to matches between real-time acceleration data and previously stored acceleration profiles, and perform other methods described herein.

The operating system 713 may be a LINUX-based operating system such as the GOOGLE mobile device platform; APPLE MAC OS X; MICROSOFT WINDOWS NT/WINDOWS 2000/WINDOWS XP/WINDOWS MOBILE; a variety of UNIX-flavored operating systems; or a proprietary operating system for computers or embedded systems. The application development platform or framework for the operating system 713 may be: BINARY RUNTIME ENVIRONMENT FOR WIRELESS (BREW); JAVA Platform, Micro Edition (JAVA ME) or JAVA 2 Platform, Micro Edition (J2ME) using the SUN MICROSYSTEMS JAVASCRIPT programming language; PYTHON™, FLASH LITE, or MICROSOFT .NET Compact, or another appropriate environment.

The device stores computer-executable code for the operating system 713, and the application programs 715 such as an email, instant messaging, a video service application, a mapping application word processing, spreadsheet, presentation, gaming, mapping, web browsing, JAVASCRIPT engine, or other applications. For example, one implementation may allow a user to access the GOOGLE GMAIL email application, the GOOGLE TALK instant messaging application, a YOUTUBE video service application, a GOOGLE MAPS or GOOGLE EARTH mapping application, or a GOOGLE PICASA imaging editing and presentation application. The application programs 715 may also include a widget or gadget engine, such as a TAFRI™ widget engine, a MICROSOFT gadget engine such as the WINDOWS SIDEBAR gadget engine or the KAPSULES™ gadget engine, a YAHOO! widget engine such as the KONFABULTOR™ widget engine, the APPLE DASHBOARD widget engine, the GOOGLE gadget engine, the KLIPFOLIO widget engine, an OPERA™ widget engine, the WIDSETS™ widget engine, a proprietary widget or gadget engine, or other widget or gadget engine the provides host system software for a physically-inspired applet on a desktop.

Although it is possible for automatic activating applications based on an analysis of real-time acceleration, it may also be possible to implement the functions described herein as a dynamic link library (DLL), or as a plug-in to other application programs such as an Internet web-browser such as the FOXFIRE web browser, the APPLE SAFARI web browser or the MICROSOFT INTERNET EXPLORER web browser.

The navigation module 717 may determine an absolute or relative position of the device, such as by using the Global Positioning System (GPS) signals, the GLObal NAvigation Satellite System (GLONASS), the Galileo positioning system, the Beidou Satellite Navigation and Positioning System, an inertial navigation system, a dead reckoning system, or by accessing address, internet protocol (IP) address, or location information in a database. The navigation module 717 may also be used to measure angular displacement, orientation, or velocity of the device 600, such as by using one or more accelerometers.

Figure 8:
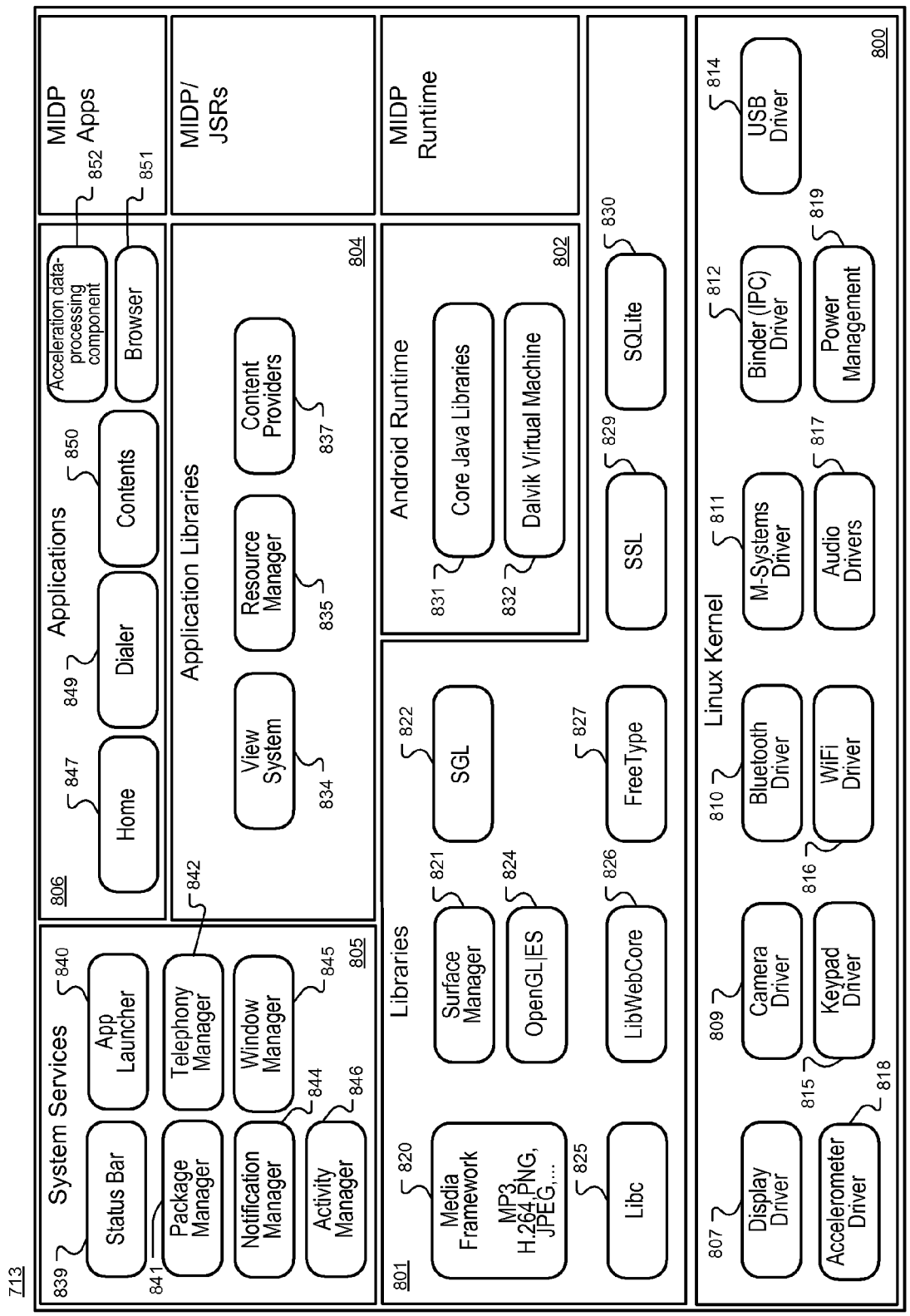
FIG. 8 is a block diagram illustrating exemplary components of the operating system used by the device of FIG. 6.

FIG. 8 is a block diagram illustrating exemplary components of the operating system 713 used by the device 600, in the case where the operating system 713 is the GOOGLE mobile device platform. The operating system 713 invokes multiple processes, while ensuring that the associated phone application is responsive, and that wayward applications do not cause a fault (or crash) of the operating system. Using task switching, the operating system 713 allows for the switching of applications while on a telephone call, without losing the state of each associated application. The operating system 713 may use an application framework to encourage reuse of components, and provide a scalable user experience by combining pointing device and keyboard inputs and by allowing for pivoting. Thus, the operating system can provide a rich graphics system and media experience, while using an advanced, standards-based web browser.

In some implementations, the operating system 713 is organized into six components: a kernel 800, libraries 801, an operating system runtime 802, application libraries 804, system services 805, and applications 806. The kernel 800 includes a display driver 807 that allows software such as the operating system 713 and the application programs 715 to interact with the display 601 via the display interface 702, a camera driver 809 that allows the software to interact with the camera 607; a BLUETOOTH driver 810; an M-Systems driver 811; a binder (IPC) driver 812, a USB driver 814, a keypad driver 815 that allows the software to interact with the keyboard 602 via the keyboard interface 704; a WiFi driver 816; audio drivers 817 that allow the software to interact with the microphone 609 and the speaker 610 via the sound interface 709; and a power management component 819 that allows the software to interact with and manage the power source 719. An accelerometer driver 818 can also be included to allow application programs to interact with an accelerometer included in the mobile device 600.

The BLUETOOTH driver, which in one implementation is based on the BlueZ BLUETOOTH stack for LINUX-based operating systems, provides profile support for headsets and hands-free devices, dial-up networking, personal area networking (PAN), or audio streaming (such as by Advance Audio Distribution Profile (A2DP) or Audio/Video Remote Control Profile (AVRCP). The BLUETOOTH driver provides JAVA bindings for scanning, pairing and unpairing, and service queries.

The libraries 801 include a media framework 820 that supports standard video, audio and still-frame formats (such as Moving Picture Experts Group (MPEG)-4, H.264, MPEG-1 Audio Layer-3 (MP3), Advanced Audio Coding (AAC), Adaptive Multi-Rate (AMR), Joint Photographic Experts Group (JPEG), and others) using an efficient JAVA Application Programming Interface (API) layer; a surface manager 821; a simple graphics library (SGL) 822 for two-dimensional application drawing; an Open Graphics Library for Embedded Systems (OpenGL ES) 824 for gaming and three-dimensional rendering; a C standard library (LIBC) 825; a LIBWEBCORE library 826; a FreeType library 827; an SSL 829; and an SQLite library 830.

The operating system runtime 802 includes core JAVA libraries 831, and a Dalvik virtual machine 832. The Dalvik virtual machine 832 is a custom virtual machine that runs a customized file format (.DEX).

The operating system 713 can also include Mobile Information Device Profile (MIDP) components such as the MIDP JAVA Specification Requests (JSRs) components, MIDP runtime, and MIDP applications as shown in FIG. 8. The MIDP components can support MIDP applications running on the device 600.

With regard to graphics rendering, a system-wide composer manages surfaces and a frame buffer and handles window transitions, using the OpenGL ES 824 and two-dimensional hardware accelerators for its compositions.

The Dalvik virtual machine 832 may be used with an embedded environment, since it uses runtime memory very efficiently, implements a CPU-optimized bytecode interpreter, and supports multiple virtual machine processes per device. The custom file format (.DEX) is designed for runtime efficiency, using a shared constant pool to reduce memory, read-only structures to improve cross-process sharing, concise, and fixed-width instructions to reduce parse time, thereby allowing installed applications to be translated into the custom file formal at build-time. The associated bytecodes are designed for quick interpretation, since register-based instead of stack-based instructions reduce memory and dispatch overhead, since using fixed width instructions simplifies parsing, and since the 16-bit code units minimize reads.

The application libraries 804 include a view system 834, a resource manager 835, and content providers 837. The system services 805 includes a status bar 839; an application launcher 840; a package manager 841 that maintains information for all installed applications; a telephony manager 842 that provides an application level JAVA interface to the telephony subsystem 720; a notification manager 844 that allows all applications access to the status bar and on-screen notifications; a window manager 845 that allows multiple applications with multiple windows to share the display 601; and an activity manager 846 that runs each application in a separate process, manages an application life cycle, and maintains a cross-application history.

The applications 806 include a home application 847, a dialer application 849, a contacts application 850, a browser application 851, and an acceleration data-processing component 852 (or suite 852 of components).

The telephony manager 842 provides event notifications (such as phone state, network state, Subscriber Identity Module (SIM) status, or voicemail status, allows access to state information (such as network information, SIM information, or voicemail presence), initiates calls, and queries and controls the call state. The browser application 851 renders web pages in a full, desktop-like manager, including navigation functions. Furthermore, the browser application 851 allows single column, small screen rendering, and provides for the embedding of HTML views into other applications.

Figure 9:
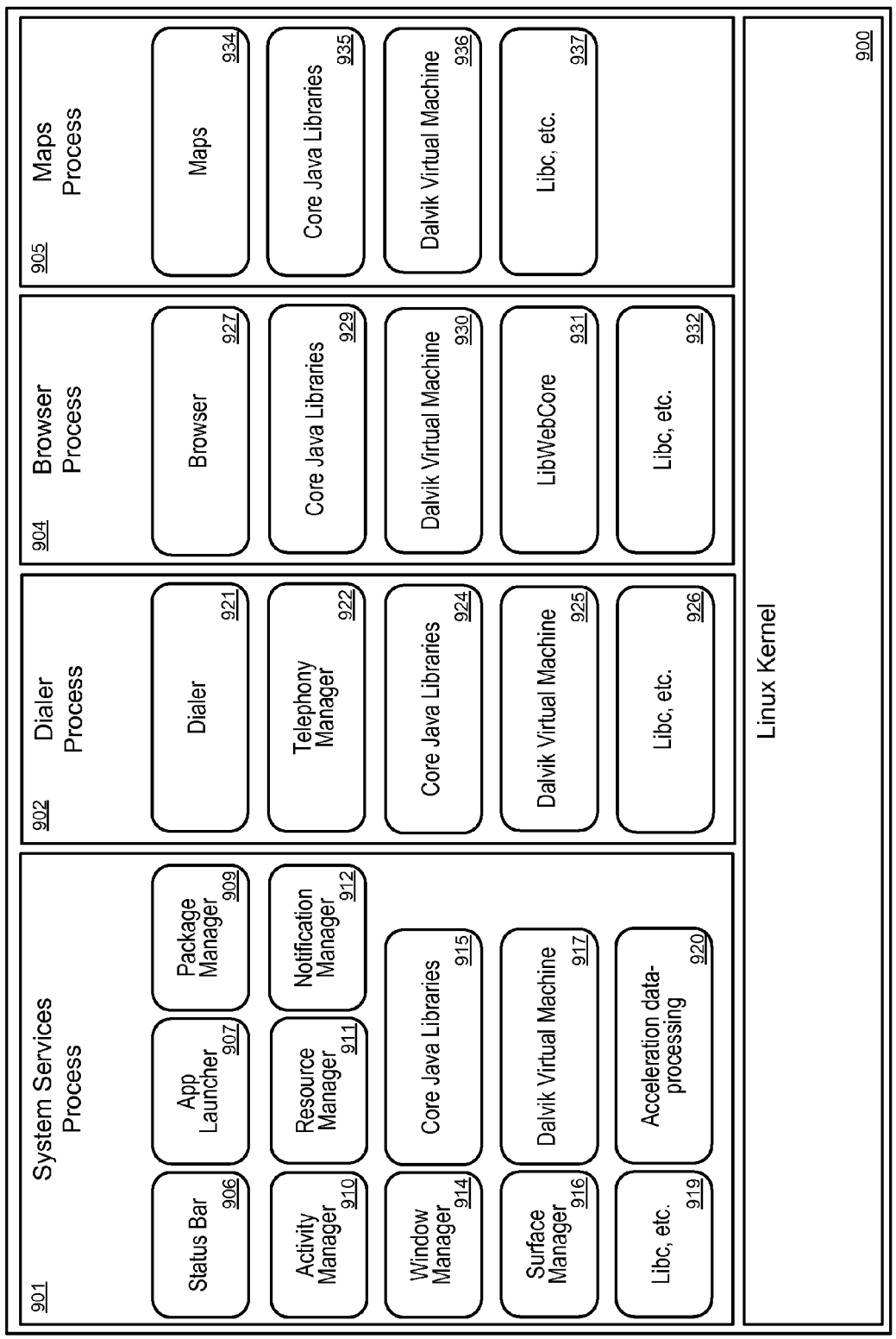
FIG. 9 is a block diagram illustrating exemplary processes implemented by the operating system of FIG. 8.

FIG. 9 is a block diagram illustrating exemplary processes implemented by the operating system kernel 900. Generally, applications and system services run in separate processes, where the activity manager 910 runs each application in a separate process and manages the application life cycle. The applications run in their own processes, although many activities or services can also run in the same process. Processes are started and stopped as needed to run an application's components, and processes may be terminated to reclaim resources. Each application is assigned its own process, whose name is the application's package name, and individual parts of an application can be assigned another process name.

Some processes can be persistent. For example, processes associated with core system components such as the surface manager 916, the window manager 914, or the activity manager 910 can be continuously executed while the device 600 is powered. Additionally, some application-specific processes can also be persistent. For example, processes associated with the dialer application 849 or the acceleration data-processing component 852 may be persistent.

The processes implemented by the operating system kernel 900 may generally be categorized as system services processes 901, dialer processes 902, browser processes 904, and maps processes 905. The system services processes 901 include status bar processes 906 associated with the status bar 839; application launcher processes 907 associated with the application launcher 840; package manager processes 909 associated with the package manager 841; activity manager processes 910 associated with the activity manager 846; resource manager processes 911 associated with a resource manager 835 that provides access to graphics, localized strings, and XML layout descriptions; notification manger processes 912 associated with the notification manager 844; window manager processes 914 associated with the window manager 845; core JAVA libraries processes 915 associated with the core JAVA libraries 831; surface manager processes 916 associated with the surface manager 821; Dalvik virtual machine processes 917 associated with the Dalvik virtual machine 832; LIBC processes 919 associated with the LIBC library 825; and acceleration data-processing processes associated with the acceleration data-processing component 852.

The dialer processes 902 include dialer application processes 921 associated with the dialer application 849; telephony manager processes 922 associated with the telephony manager 842; core JAVA libraries processes 924 associated with the core JAVA libraries 831; Dalvik virtual machine processes 925 associated with the Dalvik Virtual machine 832; and LIBC processes 926 associated with the LIBC library 825.

The browser processes 904 include browser application processes 927 associated with the browser application 851; core JAVA libraries processes 929 associated with the core JAVA libraries 831; Dalvik virtual machine processes 930 associated with the Dalvik virtual machine 832; LIBWEBCORE processes 931 associated with the LIBWEBCORE library 826; and LIBC processes 932 associated with the LIBC library 825.

The maps processes 905 include maps application processes 934, core JAVA libraries processes 935, Dalvik virtual machine processes 936, and LIBC processes 937. Notably, some processes, such as the Dalvik virtual machine processes, may exist within one or more of the systems services processes 901, the dialer processes 902, the browser processes 904, and the maps processes 905.

Figure 10:
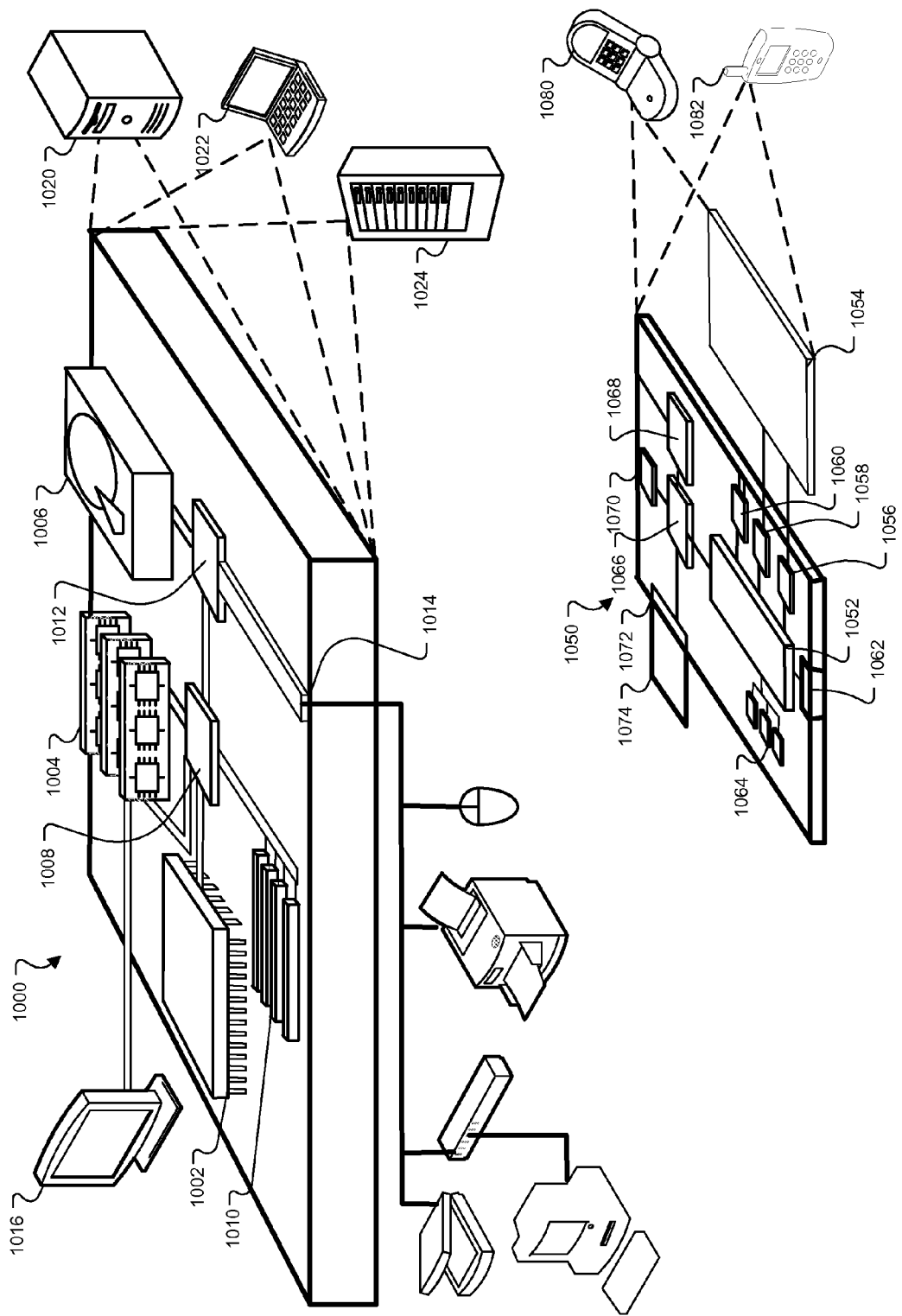
FIG. 10 shows an example of a computer device and a mobile computer device that can be used to implement the techniques described here.

FIG. 10 shows an example of a generic computer device 1000 and a generic mobile computer device 1050, which may be used with the techniques described here. Computing device 1000 is intended to represent various forms of digital computers, such as laptops, desktops, workstations, personal digital assistants, servers, blade servers, mainframes, and other appropriate computers. Computing device 1050 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 1000 includes a processor 1002, memory 1004, a storage device 1006, a high-speed interface 1008 connecting to memory 1004 and high-speed expansion ports 1010, and a low speed interface 1012 connecting to low speed bus 1014 and storage device 1006. Each of the components 1002, 1004, 1006, 1008, 1010, and 1012, are interconnected using various busses, and may be mounted on a common motherboard or in other manners as appropriate. The processor 1002 can process instructions for execution within the computing device 1000, including instructions stored in the memory 1004 or on the storage device 1006 to display graphical information for a GUI on an external input/output device, such as display 1016 coupled to high speed interface 1008. In other implementations, multiple processors and/or multiple buses may be used, as appropriate, along with multiple memories and types of memory. Also, multiple computing devices 1000 may be connected, with each device providing portions of the necessary operations (e.g., as a server bank, a group of blade servers, or a multi-processor system).

The memory 1004 stores information within the computing device 1000. In one implementation, the memory 1004 is a volatile memory unit or units. In another implementation, the memory 1004 is a non-volatile memory unit or units. The memory 1004 may also be another form of computer-readable medium, such as a magnetic or optical disk.

The storage device 1006 is capable of providing mass storage for the computing device 1000. In one implementation, the storage device 1006 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 1004, the storage device 1006, memory on processor 1002, or a propagated signal.

The high speed controller 1008 manages bandwidth-intensive operations for the computing device 1000, while the low speed controller 1012 manages lower bandwidth-intensive operations. Such allocation of functions is exemplary only. In one implementation, the high-speed controller 1008 is coupled to memory 1004, display 1016 (e.g., through a graphics processor or accelerator), and to high-speed expansion ports 1010, which may accept various expansion cards (not shown). In the implementation, low-speed controller 1012 is coupled to storage device 1006 and low-speed expansion port 1014. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1000 may be implemented in a number of different forms, as shown in the figure. For example, it may be implemented as a standard server 1020, or multiple times in a group of such servers. It may also be implemented as part of a rack server system 1024. In addition, it may be implemented in a personal computer such as a laptop computer 1022. Alternatively, components from computing device 1000 may be combined with other components in a mobile device (not shown), such as device 1050. Each of such devices may contain one or more of computing device 1000, 1050, and an entire system may be made up of multiple computing devices 1000, 1050 communicating with each other.

Computing device 1050 includes a processor 1052, memory 1064, an input/output device such as a display 1054, a communication interface 1066, and a transceiver 1068, among other components. The device 1050 may also be provided with a storage device, such as a microdrive or other device, to provide additional storage. Each of the components 1050, 1052, 1064, 1054, 1066, and 1068, are interconnected using various buses, and several of the components may be mounted on a common motherboard or in other manners as appropriate.

The processor 1052 can execute instructions within the computing device 1050, including instructions stored in the memory 1064. The processor may be implemented as a chipset of chips that include separate and multiple analog and digital processors. The processor may provide, for example, for coordination of the other components of the device 1050, such as control of user interfaces, applications run by device 1050, and wireless communication by device 1050.

Processor 1052 may communicate with a user through control interface 1058 and display interface 1056 coupled to a display 1054. The display 1054 may be, for example, a TFT LCD (Thin-Film-Transistor Liquid Crystal Display) or an OLED (Organic Light Emitting Diode) display, or other appropriate display technology. The display interface 1056 may comprise appropriate circuitry for driving the display 1054 to present graphical and other information to a user. The control interface 1058 may receive commands from a user and convert them for submission to the processor 1052. In addition, an external interface 1062 may be provide in communication with processor 1052, so as to enable near area communication of device 1050 with other devices. External interface 1062 may provide, for example, for wired communication in some implementations, or for wireless communication in other implementations, and multiple interfaces may also be used.

The memory 1064 stores information within the computing device 1050. The memory 1064 can be implemented as one or more of a computer-readable medium or media, a volatile memory unit or units, or a non-volatile memory unit or units. Expansion memory 1074 may also be provided and connected to device 1050 through expansion interface 1072, which may include, for example, a SIMM (Single In Line Memory Module) card interface. Such expansion memory 1074 may provide extra storage space for device 1050, or may also store applications or other information for device 1050. Specifically, expansion memory 1074 may include instructions to carry out or supplement the processes described above, and may include secure information also. Thus, for example, expansion memory 1074 may be provide as a security module for device 1050, and may be programmed with instructions that permit secure use of device 1050. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1064, expansion memory 1074, memory on processor 1052, or a propagated signal that may be received, for example, over transceiver 1068 or external interface 1062.

Device 1050 may communicate wirelessly through communication interface 1066, which may include digital signal processing circuitry where necessary. Communication interface 1066 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1068. In addition, short-range communication may occur, such as using a Bluetooth, WiFi, or other such transceiver (not shown). In addition, GPS (Global Positioning System) receiver module 1070 may provide additional navigation- and location-related wireless data to device 1050, which may be used as appropriate by applications running on device 1050.

Device 1050 may also communicate audibly using audio codec 1060, which may receive spoken information from a user and convert it to usable digital information. Audio codec 1060 may likewise generate audible sound for a user, such as through a speaker, e.g., in a handset of device 1050. Such sound may include sound from voice telephone calls, may include recorded sound (e.g., voice messages, music files, etc.) and may also include sound generated by applications operating on device 1050.

The computing device 1050 may be implemented in a number of different forms, as shown in the figure. For example, it may be implemented as a cellular telephone 1080. It may also be implemented as part of a smartphone 1082, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of implementations have been described. Nevertheless, it will be understood that various modifications may be made without departing from the spirit and scope of the disclosed implementations. For example, many examples are provided in the context of a mobile device, but the systems and methods described herein can also be applied to devices that are not traditionally characterized as mobile, including, for example, an in-dash vehicle navigation system or vehicle computer (which may activate different applications based on detection of stop-and-go highway traffic, smooth-flowing highway traffic, city traffic, etc.). As other examples, the systems and methods described herein can be applied to marine devices (e.g., that detect choppiness of the water or other parameters and activate applications accordingly), or consumer appliances that may activate applications in response to detecting earthquake activity, high winds, etc. Various examples have been provided in the context of activating applications, but applications can also be deactivated in response to a match between real-time acceleration data and acceleration profiles. In addition, the logic flows depicted in the figures may not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A computer-implemented method comprising:
   storing a plurality of acceleration profiles, each acceleration profile corresponding to a sequence of acceleration forces a mobile device would be subjected to when carried with a user during one of a plurality of activities corresponding to the plurality of acceleration profiles, each acceleration profile being further associated with a time at which user input was received to launch one of a plurality of user applications that are associated with the plurality of acceleration profiles;
   receiving accelerometer data from an accelerometer in the mobile device;
   correlating the accelerometer data with one acceleration profile in the plurality of acceleration profiles; and
   activating the user application of the mobile device that is associated with the correlated one acceleration profile.

2. The computer-implemented method of claim 1, wherein a particular acceleration profile of the acceleration profiles is generated based on analysis of a plurality of devices that are distinct from the mobile device.

3. The computer-implemented method of claim 2, wherein the particular acceleration profile is pre-stored in the mobile device before the mobile device is delivered to the user.

4. The computer-implemented method of claim 2, wherein the particular acceleration profile is wirelessly downloaded from a content provider to the mobile device.

5. The computer-implemented method of claim 1, wherein at least one sequence of acceleration forces is stored by the mobile device during a training mode in which actual acceleration forces to which the mobile device is subjected are sampled in real-time and stored in the mobile device.

6. The computer-implemented method of claim 1, wherein correlating comprises sampling the received accelerometer data and comparing the sampled accelerometer data to one or more of the plurality of acceleration profiles using a comparison algorithm to determine if the sampled accelerometer data matches an acceleration profile in the plurality of acceleration profiles.

7. The computer-implemented method of claim 1, wherein storing the plurality of acceleration profiles comprises storing the plurality of acceleration profiles at a network-accessible location external to the mobile device; wherein correlating the accelerometer data comprises accessing the network-accessible location after receiving the accelerometer data.

8. The computer-implemented method of claim 1, wherein correlating the accelerometer data comprises processing the accelerometer data to remove effects of positional orientation of the mobile device.

9. The computer-implemented method of claim 8, wherein processing the accelerometer data comprises translating multi-axis accelerometer data to a different coordinate system than a coordinate system in which the multi-axis data was captured.

10. A method of automatically activating an application in a mobile device that runs a plurality of applications, the method comprising:
    in a training mode:
      receiving training acceleration data for a mobile computing device,
      receiving user input to launch an application in the plurality of applications,
      generating one or more training signatures based on the received acceleration data and the user input,
      receiving additional acceleration data for the mobile computing device and additional user input to launch the application, and
      adaptively refining the one or more training signatures, wherein the training signature is further generated based on a time at which the user input is received;
    receiving accelerometer data from an accelerometer in the mobile computing device;
    generating a signature based on the received accelerometer data;
    correlating the generated signature to an acceleration profile that is stored in the mobile computing device; and
    activating an application in the mobile computing device that is associated with the acceleration profile to which the generated signature is correlated.

11. The method of claim 10, wherein correlating comprises comparing the generated signature to one or more acceleration profiles that are stored in the mobile computing device and determining when the generated signature and one of the one or more acceleration profiles match within a threshold measure of similarity.

12. The method of claim 10, wherein receiving training acceleration data comprises receiving data from the accelerometer in the mobile computing device.

13. The method of claim 12, wherein the training acceleration data comprises acceleration data for the mobile computing device in at least two axes.

14. The method of claim 13, wherein receiving training acceleration data comprises periodically receiving the training acceleration data for the mobile computing device at a rate of at least 25 Hz.

15. The method of claim 10, further comprising storing the received training acceleration data in a first-in, first-out circular buffer such that a predetermined amount of recently received training acceleration data is stored at a given time.

16. The method of claim 10, wherein the training signature is further generated based on a day of the week on which the user input is received.

17. The method of claim 10, wherein the training signature is further generated based on a location of the mobile computing device when the user input is received.

18. The method of claim 10, further comprising generating a first training signature based on the training acceleration data and the user input to launch the application being received at a first time, and generating a second, distinct training signature based on second training acceleration data and second user input to launch the application being received at a second time that is different than the first time by at least a predetermined threshold.

19. The method of claim 10, wherein generating the training signature comprises generating the training signature based on the training acceleration data being received for a predetermined period of time prior to receiving the user input to launch the application.

20. The method of claim 19, wherein generating the training signature further comprises generating the training signature based on second training acceleration data that is received for a second predetermined period of time following receiving the user input to launch the application.

21. A method of automatically activating an application in a mobile device that runs a plurality of applications, the method comprising:
receiving training acceleration data for a mobile device;
receiving user input to launch an application in the plurality of applications;
generating a training signature based on (a) the received training acceleration data, (b) the user input, and (c) a time at which the user input is received;
receiving accelerometer data from an accelerometer in the mobile device;
generating a signature based on the received accelerometer data;
correlating the generated signature to the training signature; and
activating the application in the mobile device that is associated with the training signature to which the generated signature is correlated.

22. The method of claim 21, wherein correlating comprises comparing the generated signature to one or more existing training signatures that are stored in a network-accessible device that is external to the mobile device.

23. The method of claim 21, further comprising receiving confirmation input from a user of the mobile device prior to activating the application.

24. The method of claim 21, wherein the training signature is further generated based on a day of the week on which the user input is received.

25. A system comprising:
a programmable processor; and
a computer-readable storage medium coupled to the processor and having instructions stored therein, which when executed by the processor causes the processor to perform a method that includes:
storing a plurality of acceleration profiles, each acceleration profile corresponding to a sequence of acceleration forces a mobile device would be subjected to when carried with a user during one of a plurality of activities corresponding to the plurality of acceleration profiles, each acceleration profile being further associated with a time at which user input was received to launch one of a plurality of user applications that are associated with the plurality of acceleration profiles;
receiving accelerometer data from an accelerometer in the mobile device;
correlating the accelerometer data with one acceleration profile in the plurality of acceleration profiles; and
activating the user application of the mobile device that is associated with the correlated one acceleration profile.

26. A system comprising:
a programmable processor; and
a computer-readable storage medium coupled to the processor and having instructions stored therein, which when executed by the processor causes the processor to perform a method that includes:
receiving training acceleration data for a mobile device;
receiving user input to launch an application in a plurality of applications;
generating a training signature based on (a) the received training acceleration data, (b) the user input, and (c) a time at which the user input is received;
receiving accelerometer data from an accelerometer in the mobile device;
generating a signature based on the received accelerometer data;
correlating the generated signature to the training signature; and
activating the application in the mobile device that is associated with the training signature to which the generated signature is correlated.

* * * * *